United States Patent
Boehm et al.

(12)

(10) Patent No.: US 6,569,665 B1
(45) Date of Patent: May 27, 2003

(54) CALPAINES, PRODUCTION AND USE THEREOF

(75) Inventors: Thomas Boehm, Vörstetten (DE); Neil T. Dear, Heidelberg (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 09/308,345

(22) PCT Filed: Nov. 28, 1997

(86) PCT No.: PCT/EP99/06644

§ 371 (c)(1),
(2), (4) Date: May 19, 1999

(87) PCT Pub. No.: WO98/24916

PCT Pub. Date: Jun. 11, 1998

(30) Foreign Application Priority Data

Dec. 4, 1996 (DE) .......................................... 196 50 142
Apr. 30, 1997 (DE) .......................................... 197 18 248

(51) Int. Cl.⁷ ........................... C12P 21/06; C12N 9/50; C12N 9/64; C12N 1/20; C12N 15/00
(52) U.S. Cl. ...................... 435/226; 435/183; 435/69.1; 435/219; 435/252.3; 435/254.1; 435/320; 435/325; 435/348; 536/23.2; 536/235; 536/24.1; 536/24.5
(58) Field of Search ............................... 435/320.1, 348, 435/219, 226, 69.1, 183, 253.2, 254.1, 325; 536/23.2, 23.5, 24.1, 24.5

(56) References Cited

FOREIGN PATENT DOCUMENTS

WO  WO 96/02634 A1 * 1/1996
WO  WO 96/16175 A2 * 5/1996

OTHER PUBLICATIONS

Neil Dear et al. A new subfamily of vertebrate calpains lacking a clamodulin–like domain: implications for calpain regulation and evolution. Genomics vol. 45:175–184, 1997.*
Mugita N. et al. Identification of a novel, tissue specific calpain htra–3; a human homologue of the C.elegans sex determination gene. Biochemical and Biophysical Research Communications vol. 239:845–850, 1997.*
Dear. T.N. Direct submission to GenBank. Accession No. Y10656, Jan. 20, 1997.*
Algate P.A. Direct submission to GenBank. Accession No. U85020, Jan. 10, 1997.*
Mugita et al. Direct submission to GenBank. Accession No. U94346, Mar. 18, 1997.*
Trends in Pharm. vol. 15, 1994, 412–419.
Bio. Chem., vol. 276, 9/95, 523–529.
J. Bio. Chem. vol. 268, No. 26, 19476–19482.
Febs Lts. 343, 1994 1–5.
Mol. Cell. Bio, Feb. 95, 824–834, vol. 15, No. 2.
Stroke, vol. 225, No. 3, 3/94.
Neu. Res., 1995, vol. 17, Aug., 249–258.
Proc. Natl. Acad, Sci, vol. 93, 3428–3433, 4/96.
Proc. Natl. Acad. Sci, vo. 92, 7662–7666, 8/95.
Japanese Cir. J., vol. 59, 1/95, 40–48.
Neuron, vol. 14, 651–659, 3/95, Higaki et al.
Cytokine, vol. 6, No. 6, 11/94, 597–601.
Int. J. of Oncology 5: supplement, 1994, 381.
Cir. Res., vol. 72, No. 2, 2/93, 413–423.
Bio. J., 1992, 285, 859–862.
Stroke, vol. 25, No. 3, Mar. 1994, Hong et al., pp. 663–669.
Neurological Research, 1995, vol. 17, Aug.; Bartus et al., 249–258.
Proc. Natl. Acad. Sci. USA, vol. 93, pp. 3428–3433, Apr. 1996, Neurobiology, Saatman et al.
Proc. Natl. Acad. Sci, USA, vol. 92, pp. 7662–7666, Aug. 1995, Edelstein et al.
Japanese Circulation Journal, vol. 59, Jan. 1995, Yoshida et al., pp. 40–48.
Cytokine, vol. 6, No. 6, (Nov.), 1994; pp. 597–601, Watanabe et al.
International Journal of Oncology 5: Supplement, 1994, p. 381, C–29, Shiba et al.
Circulation Research, vol. 72, No. 2, Feb. 1993, March et al., pp. 413–423.
Biochem. J. (1992) vol. 285, pp. 857–862, Suzuki et al.
Neuron, vol. 14, 651–659, Mar., 1995, Higaki et al.

* cited by examiner

*Primary Examiner*—Rebecca E. Prouty
*Assistant Examiner*—Manjunath Rao
(74) *Attorney, Agent, or Firm*—Wood, Phillips, Katz, Clark & Mortimer

(57) ABSTRACT

Novel calpains and their preparation, and methods for screening for novel calpain inhibitors and their use are described.

12 Claims, 14 Drawing Sheets

```
           YXHSXXKNEFWSALLEKAYAKLXGCYEALXGGXTXDALXDFTGGVSEXXDLXE--------XXXXLFXXL
           |    |    |    |    |    |    |    |
          220  230  240  250  260  270  280
nCL-3      YCHSNSKNEFWCALVEKAYAKLAGCYQALDGGNTADALVDFTGGVSEPIDLTEGDLATDEAKRNQLFERV 218
HHCPE79pro --------------------------------------------------------------------  2
tra-3      FARSKTPNEFWSALLEKAFAKLYGCYENLVGGHLSDALQDVSGGVAETLHVRKFLKDDPNDTELKLFNDL 218
Drosophila/ca YMHSTEKNEFWSALLEKAYAKLHGSYEALKGGSTCEAMEDFTGGVSEWYDLKE--------APGNLFTIL 266

XKAXXRGXLXXASIXAXTXXX-EAXLXCGLVKGHAYAVTXVCXIDXXXPN--G----F----K-KXXXMIRL
           |    |    |    |    |    |    |
          290  300  310  320  330  340  350
nCL-3      LKVHSRGGLISASIKAVTAADMEARLACGLVKGHAYAVTDVRKVRLGH-----GLLAFFKSEK--LDMIRL 282
HHCPE79pro ---------------------------------------------------------------------  2
tra-3      KTAFDKGALVVAAIAARTKEEIEESLDCGLVKGHAYAVSAVCTIDVTNPNERSFTSFIMGSKRKQNLIRL 288
Drosophila/ca QKAAERNSMMGCSIEPDPNVT-EAETPQGLIRGHAYSITKVCLIDIVTPNRQG-----KIPMIRM 325

RNPWG-EXEWNGPWSDXSPEWQXVSXSQXXXMGVTXX-----DDGEFWMTFEDFCRYFTDIIKCRLINTSX
           |    |    |    |    |    |    |
          360  370  380  390  400  410  420
nCL-3      RNPWG-EREWTGPWSDTSEEWQKVSKSEREKMGVTVQ-----DDGEFWMTFEDMCRYFTDIIKCRLINTSY 347
HHCPE79pro ---------------------------------------TFEDVCRYFTDIIKCRVINTSH  23
tra-3      QNPWG-EKEWNGAWSDDSPEWQNVSASQLSTMGVQPANSDSDDGDFWMPWESFVHYFTDISLCQLFNTSV 357
Drosophila/ca RNPWGNEAEWNGPWSDSSPEWRYIPEEQKAEIGLTFDR----DGEFWMSFQDFLNHFDRVEICNLSPDSL 391

FIGURE 2(B)
```

```
                                                                            490
                       430       440       450       460       470       480    |
                         |         |         |         |         |         |    |
nCL-3         LSIH------KTWEEARLHGAWTXHE----DPPQNRAGGCINHKDTFFQNPQYIFEVKKPEDE------VL 402
HHCPE79pro    LSIH------KTWEEARLHGAWTRHE----DPQQNRSGGCINHKDTFFQNPQYVFEVKKPEDE------VL  78
tra-3         LSIH------KTWEEARLHGAWTLHE----DPRQNRGGGCINHKDTFFQNPQYIFEVKKPEDE------VL 415
              FSFS------RSYDEQIVFSEWTTNGKKSGAPDDRAGGCHNFKATFCNNPQYIFDIPSPNCS------VM 453
Drosophila/ca TEDQQNSGKRKWEMSMYEGEWT--------PGVTAGGCRNFLDTFWHNPQYIITLVDPDEEGQCTVI 500       510       520       530       540       550       560
                         |         |         |         |         |         |         |
nCL-3         IALIQQRPKRSTKREGKGENLTIGFDIYKVEE----NRQYRMHSLQHKXAXS---XYINXRSVXLRXX-L
HHCPE79pro    IS-IQQRPKRSTRREGKGENLAIGFDIYKVEE----NRQYRMHSLQHKAASS---IYINSRSVFLRTE-L 463
tra-3         IC-IQQRPKRSTRREGKGENLXIGFDIYKVEE----NRQYRMHSLQHK                       121
              FALIQNDPSEGLKK--REPFVTIGMHVMKVEN----NRQYRVHTAMHPIAIS---DYASGRSVYLHLQSL 476
Drosophila/ca VALMQK--NRRSKRNMGMECLTIGFAIYSLNDRELENRPQGLNFFRYKSSVGRSPHFINTREVCARFK-L 520

570       580       590       600       610       620       630
                         |         |         |         |         |         |         |
nCL-3         PXGRYLIIPTTFXPXEXGXFXLRVFSDXXXNXXLXXXXPX---XXXL-CXXXQXVXXXXXXGX-XXXXX
HHCPE79pro    PEGRYVIIPTTFEPGHTGEFLLRVFTDVPSNCRELRLDEPPRTCWSSL-CGYPQQVAQVHVLGAAGLKDS 532
tra-3                                                                              121
              PRGRYLLIPTTFAPKEQTLFMLRVYSDEHIHFSPLTKHAPK---LGLLKCKSAQSVTRLTHGV-DFNSA 542
Drosophila/ca PPGHYLIVPSTFDPNEEGEFIIRVFSETQNN---------                               552

FIGURE 2(C)
```

Homology between 2930 and known calpain subfamilies

µ large subunit

```
human (µ) CL    CAL6  EVEWTGAWSDSSSEWNNVDPYERDQLRVK-ME    CAL9  (SEQ ID NO:28)
chicken (µ) CL        ............Q..E.E.SL.Q.IM.R-..          (SEQ ID NO:29)
2930                  .R....P...T.S..QK.DPY..EKMG.TVQD          (SEQ ID NO:30)
``` m large subunit

```
human (m) CL    CAL6  EVEWTGRWNDNCPSWNTIDPEERERLTRR-HE    CAL9  (SEQ ID NO:31)
chicken (m) CL        ........K...N.SGV...V.........-..         (SEQ ID NO:32)
rat (m) CL            Q.......K........V...V.AN..E.-Q.          (SEQ ID NO:33)
rabbit (m) CL         ..............N...V..V....AE.-..          (SEQ ID NO:34)
2930                  .R....P.S.TSEE.QKVSKS...KMGVTVQD
```

µ/m large subunit

```
chicken (µ/m) CL CAL6 QVEWTGAWSDGSSEWDNIDPSDREELQLK-ME    CAL9  (SEQ ID NO:35)
2930                  ER....P...T.E..QKVSK.E..KMGVTVQD
``` p94/nCL-1 (muscle specific)

```
human p94       CAL6  QVEWNGSWSDRWKDWSFVDKDEKARLQHQVTE    CAL9  (SEQ ID NO:36)
mouse p94             ............G...................          (SEQ ID NO:37)
chicken p94           ..........P...KSEE.N.I..EE..I....KIA.     (SEQ ID NO:38)
pig p94               ............S...................          (SEQ ID NO:39)
rat p94               ............G...................          (SEQ ID NO:40)
cow p94               ............S........Y..........          (SEQ ID NO:41)
2930                  ER..T.P...TSEE.QK.S.S.REKMGVT.QD
``` nCL-2 (stomach specific)

```
rat nCL-2       CAL6  EVEWSGAWSDNAPEWNYIDPRRKEELDKK-AE    CAL9  (SEQ ID NO:42)
2930                  .R..T.P...TSE..QKVSKSER.KMGVTVQD
```

FIGURE 3(A)

```
                    Drosophila CalpA
Dros. CalpA    CAL6    NEAEWNGPWSDSSPEWRYIPEEQKAEIGLTFDR      CAL9   (SEQ ID NO:43)
2930                   -.R..T.....T.E..QKVSKSEREKM.V.VQD Caenorhabditis elegans Calpains
tra-3          CAL6    EKEWNGAWSDDSPEWQNVSASQLSTMGVQPANSDSD   CAL9   (SEQ ID NO:44)
CPL-1                  .Q....P...N.R..RS.PD.VKQD..LKF----DH          (SEQ ID NO:45)
2930                   .R..T.P....T.E...K..K.EREK...TVQ----.
```

FIGURE 3(B)

```
1 mouse nCL-3       (SEQ ID NO:2)                                                                              —
2 human nCL-3       (SEQ ID NO:7)                                                                              —
3 nematode tra-3    (SEQ ID NO:20)                                                                             —
4 mouse m-calpain   (SEQ ID NO:52)                                                                    MAGI     4
5 human μ-calpain   (SEQ ID NO:53)                                              MSEEIITPVYCTGV                14
6 mouse p94         (SEQ ID NO:54)       MPTVISPTVAPRTGAEPRSPGPVPHPAQGKTTE                                    33
7 rat nCL-2         (SEQ ID NO:55)                                                                    MAAL     4
8 drosophila CalpA  MDDLRGFLRQAGQEFLNAAGEAAMGAAKDVVGSVINEIFIKKEADTK                                           47
   (SEQ ID NO:19)

1              MFSCAKAY--EDQNYSALKRACLRKKVLFEDPLFPATDDSLYYKG------TPG                                         46
2              ...V.P.--..........R.D.R.R......................                                             46
3              .TRSE.TRHFGN...EK.RKI.IK..QP.V.T....P.NQ..FLEQ-----RQS                                        48
4              AIKLAKDREAAEGLG.HER.IKYLN.D.ET.RNE..EAGA..Q..S...LPS..G..ELGPYSSKT                            70
5              SAQVQKQRAREL.GLGRHEN.IKYLG.D.EQ.RVR..QSGT..R.EA..PVPQ..G..DLGPNSSKT                           80
6              AGGGHPSGIYSAIISRNFPIIGVKEKTREQ.RKK..E....YL..E..PDET..F.SQKFP----                             94
7              AAGVSKQRAVAEGLG.NQN.VKYLG.DFET.RKQ..NSG..K..E...CPSA.G..DLGPGSPDT                             70
8              RVLPSIKNMRVLGEK.SSLGPYS.V.D.ETILNS..ASGS...........SNE..QFS-----RRPD                        108
                                                                           **        *

1  PTVRWKRPKDICDDPRL--FVDGISSHDLHQGQVGNCWFVAACSSLASRESLWQKVIPDWKEQEWN                                       110
2  .A..R....G..E...-.--..........................................D                                        110
3  SDIV....GELHP..H..--..E.A.PN.VT..IL........S....A.THNFK.LAQ....ADD...S                                  112
4  RGIE....TE..A..QFII--G.ATRT.IC..AL.D...LL..IA..TLN.EILAR.V.--PD.SFQ                                      132
5  YGIK....TELLSN.QFIV--..ATRT.IC...AL.D...LL..IA..TLNDT.LHR.V.--HG.SFQ                                     142
6  IQFV....PE..EN..FII--G.ANRT.IC..DL.D...L..IAC.TLN.R.LFR....--HD.SFT                                      156
7  QGIV....TEL.PN.QFIV--G.ATRT.IR..GIVD..LL..IA..TLN.K.LYR.L.--RD.SFQ                                       132
8  RHIE.L..HE.AEN.QFFV--E.Y.RF.VQ..EL.D..LL..TAN.TQESN.FFR....--A..SFE                                      170
      *                 *    *      **                  *          *
```

FIGURE 4 (A)

```
1  PEKPDSYAGIFHFNFWRFG-EWDVIVDDRLPTVNNQLIYCHSNSKNEFWCALVEKAYAKLAGCYQ    175
2  ...NA.........H.....-........VI..........R.............        175
3  .TK--HA.......R.R.....-K..E.VI..L....RDGK.LFAR.KTP....S..L....F...Y...E    175
4  ----EN........Q..QY.-....E.V.........KDGE.LFV..AEGS...S..L.........IN...E    193
5  ----NG........QL.QF.-....V....L..IKDGK.VFV..AEG....S..L.......VN.S.E    203
6  ----EN........Q...Y.-D....VI..C....Y...VFTK..HR....S..L.........H.S.E    217
7  ----KD........Q..QY.-....E.VI........K.G..LFL..EEG....S..L.........N.S.E    193
8  ----EN........R..QY.-K....II.........Y.GE.M.M..TE....S..L.........H.S.E    231
              *****  *                *** **  *** ***   *    ** *  *

1  ALDGGNTADALVDFTGGVSEPIDLTEG------DLATDEAKRNQL-------------------    214
2  ..............................F.N..T...-------------------    214
3  N.V...HLS...Q.VS.....A.TLHVR-----KFLK.DPNDTE.-------------------    212
4  T.S..A.TEGFE.....IA.WYE.RKPPPNLFKIIQKALEKGS.LGCSIDITSAADSEA----    252
5  .S...S.SEGFE......T.WYE.RKAPSDLYQIILKALE.GS.LGCSIDISSVLDMEA----    262
6  ..K....TEAME......T.FFEIKDAPSDMYKIMRKAIE.GS.MGCSIDDGTNMTYGTSPSGLNM    283
7  ..V..S.IEGFE......I..FY..KKPPENLYYIIQKALAKGS.LGCSIDVSTAAEAFA----    252
8  ..K..S.CEAME.......WY..K.APGNLFTILQKA.E..SMMGCSIEPDNVT-EA-------    290
         *                *       **

1  ---FERVLKVHSRGGLISASIKAVTAADM-------EARLACGLVKGHAYAVTDVRKVRLGH-    266
2  ----.......M.......................-------..................-    266
3  -KL.NDLKTAFDK.A.VV.A.A.R.KEEI-------------ES.D........SA.CTIDVTNP    267
4  ---------------------------VTYQK----.......S..GAEEVESSG-    276
5  ---------------------------ITEKK----.......S..GAKQVNYRG-    286
6  GELIA.MVRNMDNSL.RDSDLDPRGSD.RPSRTIVPVQY.TRMACG.......S..GLEEALFKG-    348
7  ---------------------------TTRQK----.......S..G.EEVNFHG-    276
8  ---------------------------ETPQG----.IR....SI.--KVCLIDIV    312
                                              *  ****
```

```
1 ----GLLAFFKSEK--LDMIRL RNPWG ......-EREWTGPWSDTSEEWQKVSKSEREKMGVTVQ----D DGE       322
2 ---- ---- ------ ------ ..... ......-------------------------N--------- ...       322
3 NERSFTS.IMGS.RKQNL.... ..... ...Q.. .K..N.A....D.P...N..A.QLST...QPANSDS ...D      332
4 ---- ----SLQKL..L----- ..... ...... -QV..K.N.NCPS.NT.DPEV.AN--L.ERQ---E ...       323
5 ---- ----QVVSL..M----- ..... ...... -EV....A...S.S..NN.DPY..DQ--LR.KM--E ...       333
6 ---- EKVKLV--------- ..... ...... -QV..N.S...GWKDWSF.DKD.KAR--LQKQVT-E ...         396
7 ---- RPEKL---------- ..... ...... -.V..S.A...NAP.NYIDPRRK.E--LDKKA---E ...         323
8 TPNRQGK---------IP....M ..... ...... N.A..N......S.P..RYIPEEQKAEI.L.FDR---  ..*     366
                                *            **  *                        **

CAL6                       CAL9

1 FWM TTEDMCRYFTDIKCRLINTSVLSIH------KTWEEARLHGAWTRHE---DPQQNRSGGCINH              380
2 ... ...V---------------- ...... -----------------L...R..G....              380
3 PW.SFVH....SL.Q.F..VF.FS------RSVD.QIVFSE..TNGKKSGAPDD.A....H.F              393
4 S.S.FL.HYSRLEI.N.TPDTLTCDSYK---K.KLTKMD.N.R------RGSTA...R.Y                 377
5 S.R.FM.E..RLEI.N.TPDALK.RTIR---K.NTTLYE.P.R------RGSTA...R.Y                 387
6 SVD.FVYH..KLEI.N.TADALE.DKLQ------.TVSVNE.R.V------RGCSA...R.F               450
7 S.S.FLKQVSRLEI.N.SPD.LS.EEIH---K.NLVLEN.R.-------RGSTA...L.Y                 377
8 S.Q.FLNH.DRVEI.N.SPD.LTEDQQNSGKRK..MSMYE..E......------PGVTA...R.F           424
  *** *                           *                        *** *

1 KDTFFQNPQYVFEVKKPEDE------------ ----VLIS-IQQRPKRSTRREGKGENLAIGFDIYKVEEN      434
2 ... ...I...... ..... ......------------------C----........................  434
3 .A..CN......I..DIPS.NCS--------.MFAL..ND.SEGLKK--REPFVT..MHVM..N...          446
4 PN..WM....LIKLEEEDEDEEDGGR--GCTF.VGL.KH-R.RQ.KM.ED-MHT...G..E.P.E             439
5 PATSWV....FKIRLDETD.PDDYGDRESGCSFVALM.KH-R-R-E..F.RD-MET...AV.E.PPE           451
6 P...WI....RLKLLEED.DPE--DSEVICSF.VALM.KN-R.KDRKL.AN-LFT...A..E.PKE            512
7 PG.YWT....FKIHLDEVDEDQEEGTSEPCCT..LGLM.KN-R.RQK.I.Q.-M.S..YAV.QIPKE           441
8 L...WH.....IITLVD.DE.DEEGQ----CT.IVALM.KN-R..KRNM.ME-C.T...A...SL--          482
                                              **
```

FIGURE 4(C)

```
 1  ----------RQYRMHSLQHKAASSIYINSRSVFLRTE-LPEGRYVIIPTTFEPGHTGEF-LLRVF        488
 2  ..........       .............D-Q.........................-M...Y        488
 3  ........V.TAM.PI.I.D.ASG...Y.HLQS..R...LL......A.KEQTL.-M...Y           501
 4  LTGQTNIHLGKNFFLTT-RARER.DTF..L.E.LN.FK-...P.E..LV.S....HKD.D.-DI..       502
 5  LVGQPAVHLK.DFFLAN-ASR.R.EQF..L.E.ST.FR-...PGE..VV.S....NKE.D.-VL.F.      514
 6  MHGNKQ-HLQKDFPLYN-ASK.R.KT...M.E.SQ.FR-...PSE..IV.S.Y..HQE..-IL...       574
 7  LESHTDAHLG.DFFLGR-.PSTC..T.M.L.E.SS.VR-...P.Q.LVV.S....FKD.D.-CL...      504
 8  DRELENRPQGLNFFRYK-SSVGR.PHF..T.E.CA.FK-..P.H.L.V.S..D.NEE...FII..        545
                       *    *          *      *     *    *    *  *

1  CVGARASDRMIHYPMLG
    ▶
 1  TDVPSNCRELR-----------------------------------------------------         499
 2  ...........-----------------------------------------------------         499
 3  SDEHIHFSP.T-----------------------------------------------------         512
 4  SEKKADYQAVDDEIE-------------------------------------------------         517
 5  SEKSAGTV..DDQIQ-------------------------------------------------         529
 6  SEKRNLSE.AENTISVD-------------RPVKKKKNKPIIFVSDRANSNKEL-------GVDQE        620
 7  SEKKAKAL.IGDTVS-------------------------------------------------         519
 8  SETQN.ME.NDDHVGYGGKADTITPGFPTPKPIDPQKEGLRRLFDSIAGKDMEVDWMELKRILDHS        611
    RTSRQ

1  ----------------------------------------LDEPPRTCWSSLCGYPQQVA----------QVH     522
 2  ................................................H.........----------L.T... 522
 3  ................................................KHA.KLGLLK--..KSA.S.T-----RLT 533
 4  ----------------ANIEEIDA-NEEDI.DGF.RLFVQ.A.EDAEISAFELQTILRRVLAKRQD             566
 5  ----------------ANLPDEQVLSEEEI..NFKALFRQ.A.EDMEISVKELRTILNRIISKRKD             579
 6  AEEGKDKAGPEKRGETPQPRPGHTDQESEEQQF.NIFRQIA.DDMEICADELKNVLNTVVNKHKD              686
 7  ---------------GHPHEPHPRDMDEE..HV.SLFEEFV.KDSEISANQLKRVLNEVLSKRTD              569
 8  MRDDLPKPVVFNRFSNNMAFETQAAGPGDDGAGACGLL.LI..PFLK--GTPFEEQLGMNDQSNKR             675
```

FIGURE 4 (D)

```
1  VLGAAGLKDSPTGANS------------YVIIKCEGE-KVRSAVQRGTST---PEYNV------KGIFY     569
2  ................------------.........-...........D--------.....------.....     569
3  IH.V-DFNSAS..THNV-----------.........-.K.........-.........------QFL.H     581
4  I-------------------------.A.L.DSRK-SF.TKTLS.VKS---IQWDE------.....     612
5  L-------------------------KSDGFS.ET.KIMVDMLDEDGS.--KLGLK.FYILWTKIQKYQK.YR   625
6  L-------------------------RTKGFSLES.RSMVNLMDRDGN.--KLGLV.F.ILWNRIRNYLS..R   732
7  M-------------------------KTQGFTLES.RSMIALMDTDGS.--RLNLQ.FHHLWKKIKAWQK..K   615
8  LI.DNPADGG.VT..AIVDETHGFSKDV.RSMVAMLD.DKS.--KLGFE.FETLLSEIAKW.A..K     739
                                                *

1  RKKLAQPITVQVWNHRV-L-KDEFLGQVHLKTAPDD--LQDLHTLHLQD-----------RSSRQ     619
2  ........S.......-.-...........-.-...AD..N--.A.....R.-----------..NS..     619
3  KS.NR.QYKIE..ED.K-MAR.HL.A.SVIIALI.N--ENRDT..Q.T.------PR----     628
4  EIDVDRSG.MNSYEM.KA.EEAG.KLPCQ.HQVIVARFAD.ELIIDFDNFVRCLVRLETLFKIFK.     678
5  KFD.DKSGSMSAYEM.MAIESAG.KLNKK.YELIITRYSEPDLAVDFDNFVCCLVRLETMF.FFKT     691
6  HYDTDHSG.INSYEM.NAVNDAG.HLNSQ.YDIITMRYADKHMNIDFDSFICCFVRLEGMF.AFNA     798
7  EMDHNHVG.IEAHEH.TA.K.AG.TLNNQVQQTIAMRYACSKLGVDFNGFVACMIRLETLFKLF.L     681
8  VYDVENTGR.SGFQL.EA.NSAGYHLNNRVLNVLGHRYGSRDGKIAFD.FIMCAVKIKTYIDIFKE     805
                        *

1  -PSDLPGIVAVRVLCSASL-TAV                                              640
2  -..N...T...HI.S.???-???                                              640
3  --GTVI.T.S.T.SAFDDP-MYL                                              648
4  -LDPENTGTIQLN.A.WLSFSVL                                              700
5  LDT..D.V.TFDLFKWLQ.-.MFA                                             714
6  FDK.GD..IKLN..EWLQ.-.MYA                                             821
7  LDK.QN...QLSLAEWLC-CVL.                                              703
8  RDTEKNETATFTLEEWIER-.IYS                                             828
```

FIGURE 4(E)

CALPAINES, PRODUCTION AND USE THEREOF

The invention relates to novel calpains and to their preparation. The invention furthermore relates to methods for screening for novel calpain inhibitors and to their use.

Calpains belong to the intracellular, non-lysosomal enzymes of the cysteine protease group. They are involved in $Ca^{2+}$-dependent signal transduction in eukaryotic cells, ie. they control cellular functions depending on the $Ca^{2+}$ concentration. Calpains occur ubiquitously in animal tissues and cells from, for example, humans, chickens, rabbits or rats. Calpains have also been found in lower animals, for example in *Drosophila melanogaster* or *Caenorhabditis elegans*. No calpains have yet been detected in yeasts, fungi or bacteria.

To date, three main isoforms of these ubiquitous calpains have become known and are distinguished in vitro by their calcium-dependent activability. Calpain I (=$\mu$calpain) is activated by $\mu$-molar calcium ion concentrations, while calpain II (=mcalpain) is activated only by millimolar concentrations of calcium ions. Both calpains consist of two subunits, one large subunit of about 80 kDa and one small subunit of about 30 kDa. Both subunits of the active heterodimer have binding sites for calcium. The large subunit is composed of the following four protein domains (=I–IV): a protease domain (=domain II), a calcium-binding domain (=domain IV) and two other domains (=domain I and III) whose function is unclear. The small 30 K 30 subunit consists of a calcium-binding subunit (=IV') and of another subunit (=V) whose function is unclear. In addition to these two calpain types, a third type, which is intermediate with respect to calcium activation (=$\mu$/m 80K), has been found in chickens (Wang K. K. W. et al., TiPS, Vol. 15, 1994: 412–419, Suzuki, K et al., Biol. Chem. Hoppe-Seyler, Vol. 376, 1995: 523–529).

Besides these ubiquitously occurring calpains, recently two new calpains whose expression is tissue-specific have been identified. nCL-1 (=p94) is a muscle-specific calpain which occurs in chickens, rats and humans and which might be active as monomer and consists only of the 80 kd subunit. Besides nCL-1 there is a stomach-specific calpain which may occur in two splicing variants nCL-2 and nCL-2'. nCL-2' differs from nCL-2 by the absence of the calcium-binding region (Sorimachi, H. S. et al., J. Biol. Chem. Vol. 268, No. 26, 1993: 19476–19482, Sorimachi, H. S. et al., FEBS Lett. 343, 1994: 1–5). A calpain-homologous protein (=CalpA) which interacts with actin and presumably plays an important part in embryonic development, and which displays two different splicing variants, has also been found in Dorosophila (Mol. Cell. Biol. Vol. 15, No. 2, 1995: 824–834). In this case too, the shorter variant lacks the calcium-binding site.

It is presumed that calpains play important parts in various physiological processes. A large number of cytoskeletal, membrane-bound or regulatory proteins such as protein-kinase C, phospholipase C, spectrin, cytoskeletal proteins such as MAP2, muscle proteins, neurofilaments and neuropeptides, platelet proteins, epidermal growth factor, NMDA receptor and proteins involved in mitosis, and other proteins, are calpain substrates (Barrett M. J. et al., Life Sci. 48, 1991: 1659–69, Wang K. K. et al., Trends in Pharmacol. Sci., 15, 1994: 412–419). The normal physiological function of the calpains is stil not even now clearly understood.

Elevated calpain levels have been measured in various pathophysiological processes and diseases, for example in: ischemias of the heart (eg. myocardial infarct), of the kidney or of the central nervous system (eg. stroke), inflammations, muscular dystrophies, cataracts of the eyes (gray cataract), injuries to the central nervous system (eg. trauma), Alzheimer's disease, HIV-induced neuropathy, Parkinson's and Huntigton's [sic] diseases etc. (see Wang K. K. above). It is presumed that these diseases are connected with an elevated and persistent intracellular calcium level. This results in overactivation of calcium-dependent processes which are then no longer subject to physiological regulation. Accordingly, overactivation of calpains may also induce pathophysiological processes.

It has therefore been postulated that inhibitors of calpain enzymes may be useful for treating these diseases. Various investigations have confirmed this. Thus, Seung-Chyul Hong et al. (Stroke 1994, 25 (3), 663–669) and Bartus R. T. et al. (Neurological Res. 1995, 17, 249–258) show that calpain inhibitors have a neuroprotective effect in acute neurodegenerative disorders occurring after stroke. Likewise, calpain inhibitors improve the recovery from the memory deficits and neuromotor disturbances occurring after experimental brain traumas (Saatman K. E. et al., Proc. Natl. Acad. Sci. USA, 93, 1996: 3428–3433). Edelstein C. L. et al. (Proc. Natl. Acad. Sci. USA, 92, 1995, 7662–7666) found a protective effect of calpain inhibitors on hypoxia-damaged kidneys. Yoshida K. I. et al. (Jap. Circ. J. 59 (1), 1995, 40–48) were able to show beneficial effects of calpain inhibitors after cardiac damage caused by ischemia or reperfusion. Since calpain inhibitors inhibit the release of β-AP4 protein, a potential use for treating Alzheimer's disease has been proposed (Higaki J. et al., Neuron, 14, 1995: 651–659). The release of interleukin-1α is likewise inhibited by calpain inhibitors (Watanabe N. et al., Cytokine, 6 (6), 1994: 597–601). It has furthermore been found that calpain inhibitors show cytotoxic effects on tumor cells (Shiba E. et al., 20th Meeting Int. Ass. Breast Cancer Res., Sendai Jp, 1994, 25th–28Sept., Int. J. Onco. 5 (Suppl.), 1994, 381). Calpain also plays an important part in restenosis and in arthritis, and calpain inhibitors may have a beneficial effect on the pathology (March K. L. et al. Circ. Res. 72, 1993: 413–423, Suzuki K. et al., Biochem J., 285, 1992: 857–862).

Further possible uses of calpain inhibitors are to be found in Wang K. K. (Trends in Pharmacol. Sci., 15, 1994: 412–419).

The most potent and selective calpain inhibitor is the naturally occurring intracellular protein calpastatin. It inhibits both calpain I and calpain II, but not other cysteine proteases or thiol proteases such as cathepsin B, L or papain. However, the disadvantage of calpastatin, which consists of about 700 amino acids, is that because of the size and the inability to pass through the cell membrane it is unsuitable for possible therapies. Besides calpain inhibitors which are low molecular weight peptides, a number of non-peptide inhibitors has been identified. The disadvantages of these inhibitors are that they are unstable, are rapidly metabolized and, in some cases, are toxic. Many calpain inhibitors additionally display insufficient selectivity, ie. they inhibit not only calpain I and II but also other cysteine proteases such as papain, chymotrypsin, elastase or cathepsin B and L.

Thus there still remains a need for selective, highly effective calpain inhibitors. Highly specific test systems which allow selective inhibitors to be identified are needed to screen for these selective, highly effective calpain inhibitors. These screening tests are normally carried out with the ubiquitously occurring calpains I and II.

To find selective inhibitors, it is necessary and desirable to provide for testing further calpains which are, if possible, expressed tissue-specifically so that the inhibitors can be tested for their selectivity between the individual calpains.

In addition, further new calpains are sought-after proteins because it is highly probable that they are expressed differently in different pathologies or diseases and play an important part in these diseases.

It is an object of the present invention to provide means for profiling and identifying calpain inhibitors which make it possible to identify calpain inhibitors which, on the one hand, have an inhibitory effect on only one calpain and, on the other hand, have an inhibitory effect on several calpains, and to provide these as a therapeutic target.

We have found that this object is achieved by a novel calpain and its allelic variants, analogs or derivatives.

The invention also relates to a method for identifying calpain inhibitors, wherein the calpain nCL-3 encoded by the sequence SEQ ID NO:1 or SEQ ID NO:6 is isolated from tissues or cells in which the enzyme nCL-3 is expressed, and the inhibition of the cleavage of a substrate of the enzyme nCL-3 and, in at least one other test, the inhibition of the cleavage of a substrate of the enzymes calpain I and/or II by test substances are measured, and the test substances which show an inhibitory effect on at least one of the calpains are selected, or the test substances which do not inhibit the enzyme nCL-3 but the enzymes calpain I and/or II or which inhibit the enzyme nCL-3 but not the enzymes calpain I and/or II or which inhibit nCL-3 and the enzymes calpain I and/or II are selected.

The invention furthermore relates to a method for identifying calpain inhibitors which comprises determining the inhibition of the cleavage of a substrate of the enzyme nCL-3 or of calpains I and/or II by test substances in cellular systems, and selecting those test substances which pass through the cell membrane and which inhibit the intracellular activity of the enzyme nCL-3 and/or of the calpains I and/or II.

BRIEF DESCRIPTION OF THE FIGURES

FIGS. 3A–3B gives a comparison of the homology exhibited between the nCL-3 clone 2930 and fragments from various calpain subfamilies. Human ($\mu$)CL is given in SEQ ID NO:28, chicken ($\mu$)CL in SEQ ID NO:29, and the homologous portion of clone 2930 in SEQ ID NO:30. In the m large subunit comparison, human (m)CL is given in SEQ ID NO:31, chicken (m)CL in SEQ ID NO:32, rat (m)CL in SEQ ID NO:33, rabbit (m)CL in SEQ ID NO:34. The chicken ($\mu$/m)CL subunit is given in SEQ ID:35. Human p94/nCL-1 is given as SEQ ID NO:36, mouse p94/nCL-1 as SEQ ID NO:37, chicken p94/nCL-1 as SEQ ID NO:38, pig p94/nCL-1 as SEQ ID NO:39, rat p94/nCL-1 as SEQ ID NO:40, and cow p94/nCL-1 as SEQ ID NO:41. A portion of rat nCL-2 is given in SEQ ID NO:42. Drosophila CalpA is given in SEQ ID NO:43. The *C. elegans* calpains tra-3 and CPL-1 are given in SEQ ID NO:44 and SEQ ID NO:45, respectively.

FIGS. 4A–4E demonstrates homology between mouse nCL-3 (SEQ ID NO:2), human nCL-3 (SEQ ID NO:7), nematode tra-3 (SEQ ID NO:20), mouse m-calpain (SEQ ID NO:46), human p-calpain (SEQ ID NO:47), mouse p94 (SEQ ID NO:48), rat nCL-2 (SEQ ID NO:49), and Drosophila CalpA (SEQ ID NO:19).

Using calpain-specific primers and using genomic DNA in domain fingerprinting (Boehm T., Oncogene 8, 1993: 1385–1390), calpain-specific sequence signatures were produced by the PCR technique, and they advantageously also contain intron sequences to improve differentiation of the calpain sequences.

The redundant PCR primers specified in Table 1 were used in the cloning of the gene for nCL-3.

TABLE 1

Redundant PCR primers used for cloning nCL-3 (=2930)

| Name | Sequence | |
|---|---|---|
| CAL1 | 5<<- tng gng att gtt ggc tnc t - 3<< | (SEQ ID NO:8) |
| CAL2 | 5<<- ctn gaa aaa gcn tat gcn aa - 3<< | (SEQ ID NO:9) |
| CAL3 | 5<<- ttt ngc ata ngc ttt ttc na - 3<< | (SEQ ID NO:10) |
| CAL4 | 5<<- gtn aaa ggn cat gcn tat ac - 3<< | (SEQ ID NO:11) |
| CAL5 | 5<<- gag tan gca tgn cct ttn ac - 3<< | (SEQ ID NO:12) |
| CAL6 | 5<<- ttn cgn aat ccn tgg gg - 3<< | (SEQ ID NO:13) |
| CAL7 | 5<<- ccc can gga ttn cgn aan cg - 3<< | (SEQ ID NO:14) |
| CAL8 | 5<<- gat ggn gaa ttt tgg atg - 3<< | (SEQ ID NO:15) |
| CAL9 | 5<<- gac atc caa aat tcn cca tc - 3<< | (SEQ ID NO:16) |
| CAL10 | 5<<- nag att aca tat ttc na - 3<< | (SEQ ID NO:17) |

It was possible using the primer pair Cal6 and Cal9 (see Tab. 1) to prepare a clone designated 29/30 (=2930). This clone codes for [sic] a gene whose product was, as a novel calpain, designated nCL-3. The nucleic acid sequence of the clone 29/30 (=nCL-3 or 2930) is to be found in sequence SEQ ID NO:1. The derived amino acid sequence of the calpain nCL-3 is to be found in sequence SEQ ID NO:2. The amino acid sequence deduced taking account of the presence of an intron displays a typical calpain signature, assignment to the known calpain subfamilies of $\mu$calpain, mcalpain, nCL-1 or nCL-2 being impossible because of the low degree of homology (see Tab. 2). The homology with known calpain subfamilies is to be found in FIG. 3. Calpain nCL-3 is a novel and previously undisclosed calpain.

Sequence analyses showed the typical three amino acid residues (Cys81, His 252 and Asn284) of the catalytic center of cysteine proteases. The amino acid residues 75–86 (QGQVGNCWFVAA) (SEQ: ID NO:18) derived from the gene sequence agree with the conserved pattern of typical thiol proteases.

TABLE 2

Homology (%) at the amino acid level between mouse nCL-3 (=2930) and other calpains

| Name | % Homology |
|---|---|
| Nematode tra-3 | 34.5 |
| Drosophila CalpA | 31.5 |
| Chicken p94 | 31.2 |
| Human p94 | 30.9 |
| Mouse p94 | 30.5 |
| Rat p94 | 30.0 |
| Chicken μ/m | 28.8 |
| Chicken m | 27.8 |
| Human m | 27.3 |
| Chicken μ | 25.4 |
| Pig p94 | 25.4 |
| Rat m | 24.4 |
| Rat nCL-2 | 23.9 |
| Nematode CPL1 | 23.6 |
| Human μ | 23.1 |
| Schistosoma | 21.7 |
| Rabbit m | 16.1 |
| Pig m | 15.8 |
| Pig μ | 15.6 |
| Mouse CAP4 | 13.7 |
| Rabbit μ | 12.9 |

The intron shown in sequence SEQ ID NO:5 (from nucleotide 109 to 514) was established by comparing with the cDNA.

Figure 2:
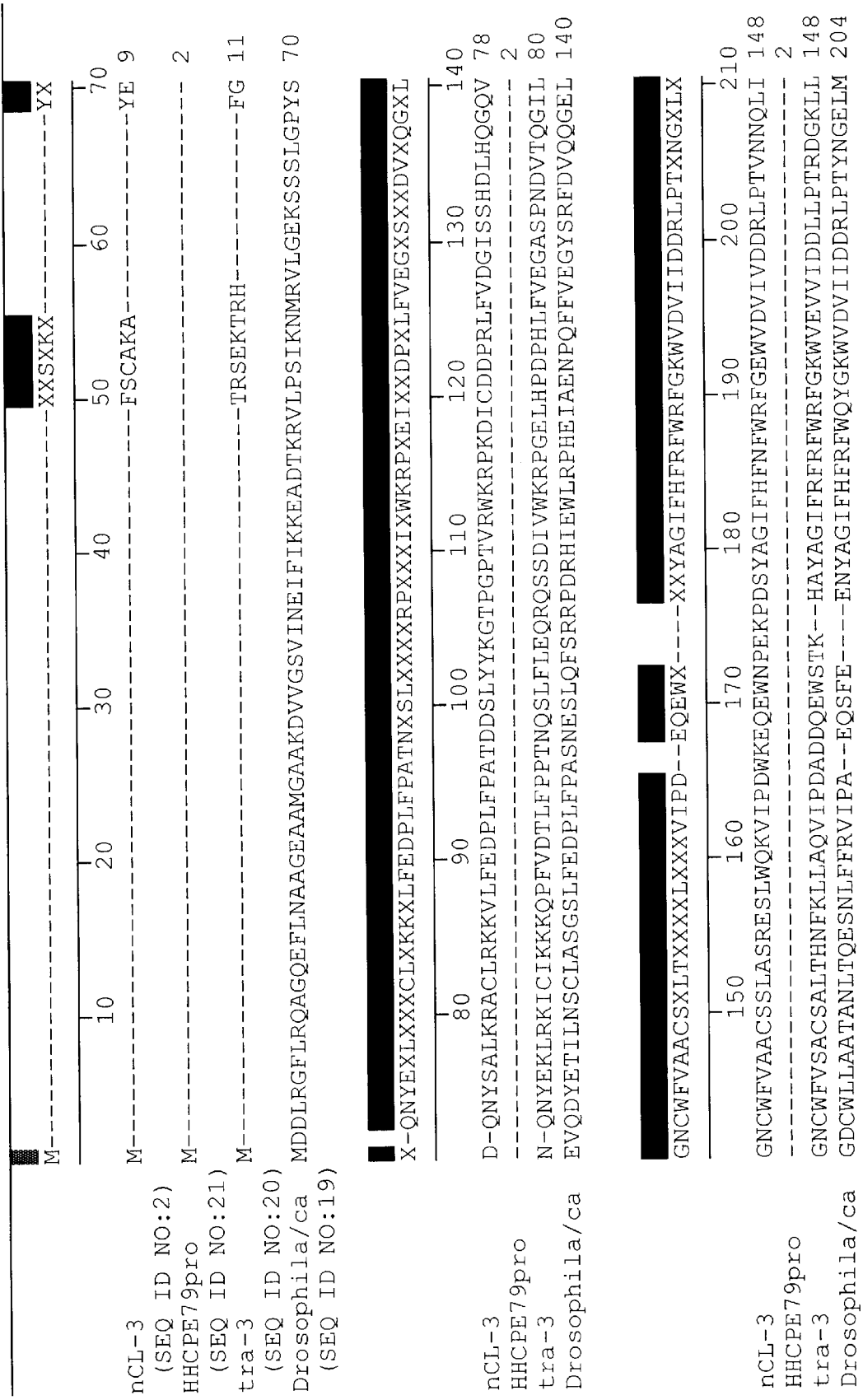
FIGS. 2A–2D, is a comparison of Drosophila CalpA (SEQ ID NO:19), Caenorhabditis Tra-3 (SEQ ID NO:20), *Homo sapiens* cDNA clone HHCPE79 (designated EST01106) (SEQ ID NO:21) and *Mus musculus* nCL-3 (SEQ ID NO:2).
Figure 2D:
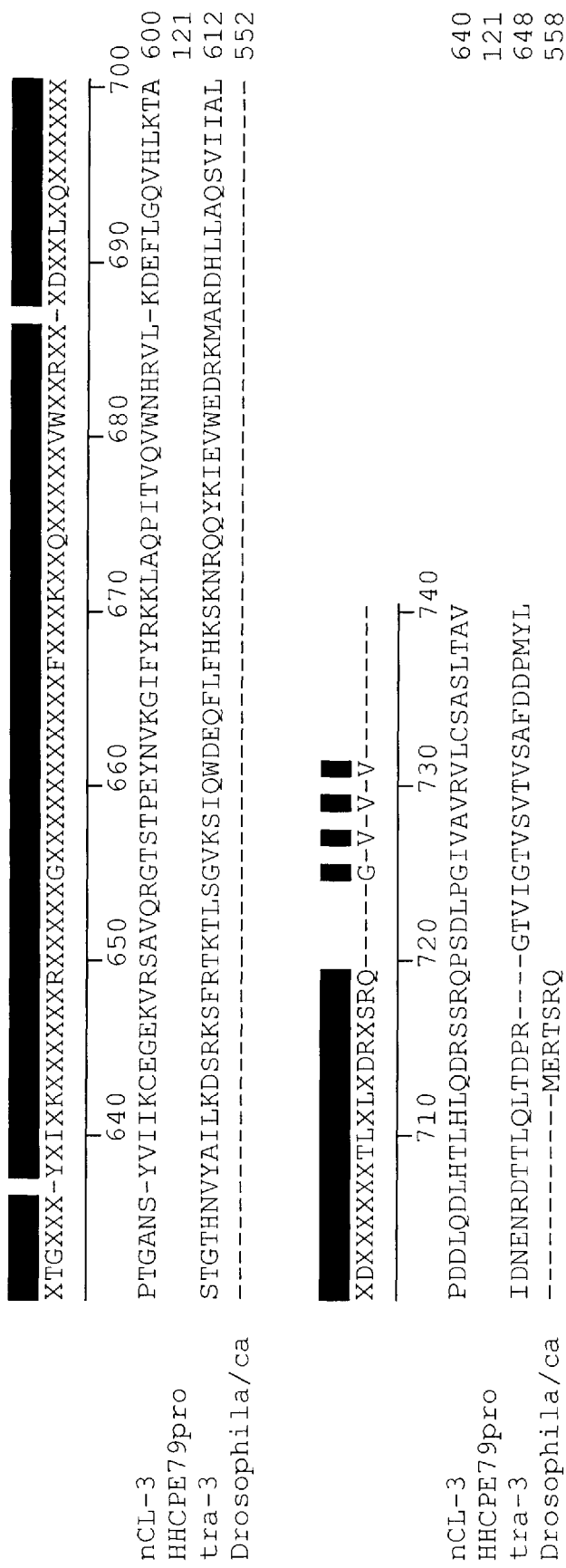

Comparison with the mouse 29/30 sequence (nCL-3) in a wide variety of databanks such as Genbank.nr and Genbank.dbest revealed homologies with CalpA (SEQ ID NO:19), Tra-3 (SEQ ID NO:20) and a human sequence designated EST01106 Homo sapiens cDNA clone HHCPE79 (SEQ ID NO:21) (see FIG. 2). The DNA and amino acid sequences were examined for homology with nonredundant nucleic acid, protein and EST databanks at the National Center of Biotechnology Information (http://www.ncbi.nlm.nih.gov). The amino acid sequence comparisons were carried out with Clustal W (Thompson et al. Nucl. Acids Res. 22, 1994, 4673–468=).

By comparison with the other calpains (FIG. 2), nCL-3 has not only a truncated domain I but also a modified C-terminal end which has no pronounced homology with domain IV of the other calpains. The consensus sequence of the $Ca^{2+}$-binding site of the calpains (called the EF hand) is located in the region of domain IV. This $Ca^{2+}$-binding site is missing from nCL-3, which possibly means that no $Ca^{2+}$ is bound to domain IV and the protein is activated in another way. It is thus the only vertebrate calpain which lacks the calmodulin-like domain IV.

CalpA is a tissue-specific expressed calpain homolog of drosophila (Theopold V. et al., Mol. Cell. Biol., Vol. 15, No. 2, 1995: 824–834). It is expressed in some neurons of the central nervous system, in scattered cells in the midgut and in blood cells of drosophila. Two different splicing variants of CalpA have been found. The shorter variant lacks the calpain-typical calcium-binding site.

The homology at the amino acid level between CalpA and nCL-3 is 31.5% (see Tab. 2).

Tra-3 is involved in sex determination in Caenorhabditis elegans. In a cascade of several genes and their products, tra-3 contributes to deciding whether caenorhabditis males or hermaphrodites develop (Kuwabara P. E. et al., TIG, Vol. 8, No. 5, 1992: 164–168). Tra-3 appears to be involved in spermatogenesis.

The homology at the amino acid level between tra-3 and nCL-3 is 34.5% (see Tab. 2). It is possible that nCL-3 is also involved in sex determination.

Other homologies between nCL-3 and other calpains are to be found in Table 2.

The greatest homology exists between nCL-3 and the human part-sequence EST01106. The part-sequence EST01106 was obtained from a hippocampus library. Nothing is known about the function (Nature 355, 6361, 1992: 632–634). The complete gene sequence and whether the sequence is a calpain gene are likewise unknown.

Sequence comparisons between CalpA (SEQ ID NO:19), Tra-3 (SEQ ID NO:20), EST01106 (SEQ ID NO:21) and nCL-3 are depicted in FIG. 2.

Starting from human hippocampus Marathon-Ready cDNA (Clontech) it was possible with the aid of a modified RACE method (=rapid amplification of cDNA ends) of Frohman et al. (Proc. Natl. Acad. Sci. USA 85, 1988, 8998–9002) and Edwards et al. (Nucl. Acids Res. 19, 1991, 5227–5232), using the abovementioned primers (Cal6 and Cal9), to clone the complete, sequence of the clone EST01106. Although the 3' region could initially not be cloned using the reverse primer of the Clontech kit. It was possible to clone the 3' end only on use of a primer complementary to the human EST sequence and of a reverse primer complementary to the cDNA sequence of the last 6 amino acids of the mouse nCL-3 sequence (5'-tcagacagccgtgagagagg-3') (SEQ ID NO:22).

The amino acid sequence (SEQ ID NO:7) derived from the gene sequence SEQ ID NO:6 shows 92.2% homology with the mouse nCL-3 sequence (see FIG. 4). This similarity corresponds to the homology at the amino acid level between the human and the mouse m-calpain (97%) and the human and the mouse p94 (93.5%), shown by our sequencings. EST01106 is thus very probably the human ortholog of the mouse nCL-3 sequence. FIG. 4 also shows the sequences of caenorhabditis tra-3, drosophila CalpA, mouse p94, mouse m-calpain, human μ-calpain and rat nCL-2. Amino acids showing agreement between various calpains and nCL-3 are indicated by dots. Dashes indicate gaps introduced to achieve maximum agreement of the sequences. The C-terminal ends of the alternative splicing products of the nCL-3 and CalpA transcripts are indicated above and below the relevant complete sequence, starting where the different sequence begins. Asterisks indicate the residues conserved in all calpains. The two amino acid sequences corresponding to the oligonucleotides Cal6 and Cal9 have been indicated by boxes. Arrows mark the splite sites of the corresponding mouse nCL-3 DNA.

Figure 5:
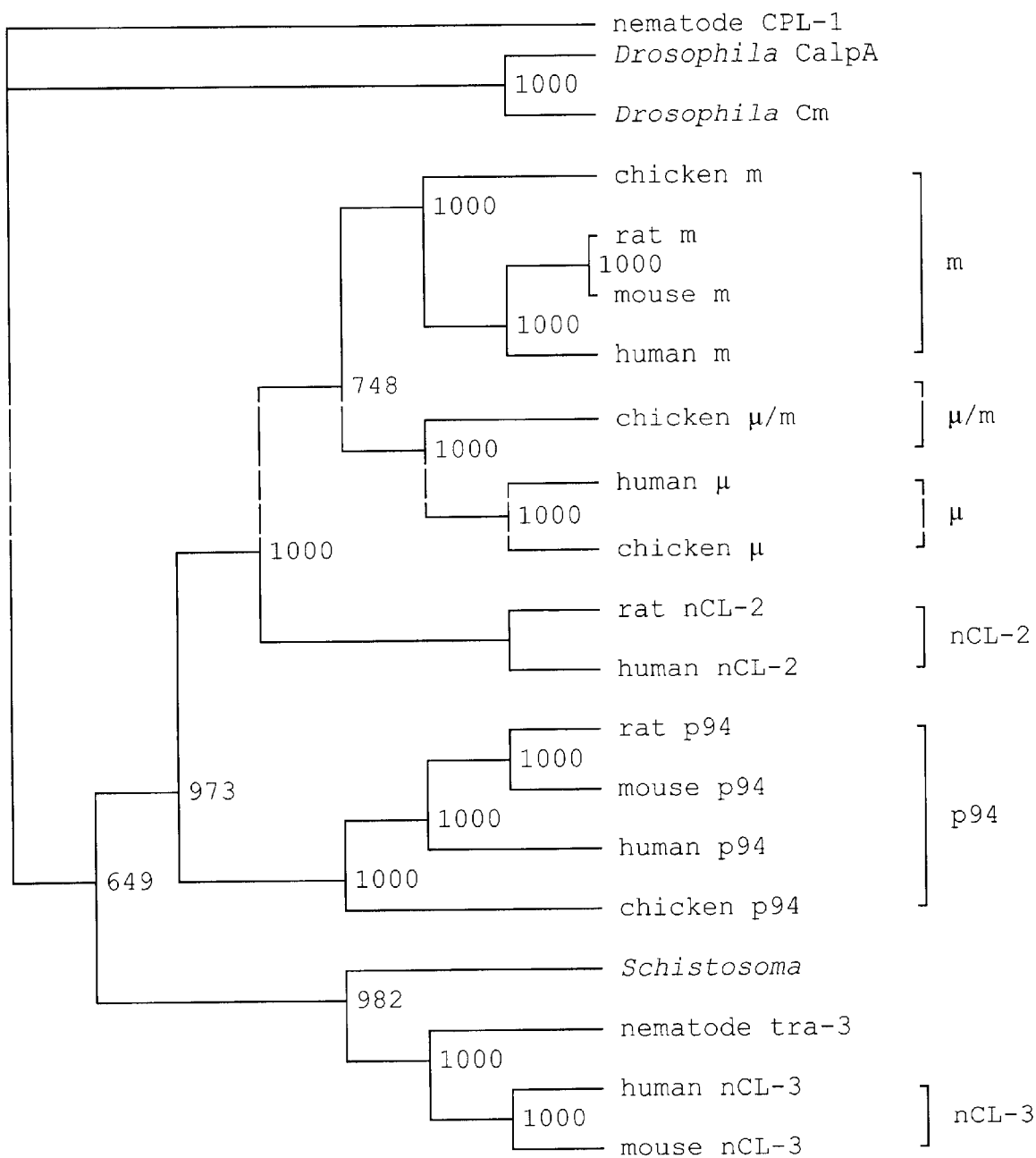
FIG. 5 represents the phylogenetic pedigree of the various calpains.

FIG. 5 represents the phylogenetic pedigree of the various calpains. The phylogenetic analyses for drawing up this pedigree were carried out using the nearest neighbor method (Saitou et al. Mol. Biol. Evol. 4, 1987, 406–425) excluding the gaps. It was possible with the aid of these phylogenetic analyses to divide the vertebrate calpains into six different groups (FIG. 5, right-hand side). The invertebrate calpains can be assigned as nearest neighbor to the nCL-3 group or are in their own group. The nCL-3 genes thus form their own group of calpains having a greater similarity to invertebrate calpains than to vertebrate calpains. The length of the horizontal lines is proportional to the phylogenetic distance between the various calpains. The length of the vertical lines has no significance. The sequences used to draw up the phylogenetic pedigree have the following SWISSPROT and EMBL numbers (accession numbers): human m (P17655), μ (P07384), p94 (P20807); rat m (Q07009), nCL-2 (D14480), p94 (P16259); mouse p94 (X92523); chicken m (D38026), μ (D38027), μ/m (P00789), p94 (D38028); nematode tra-3 (U12921); drosophila CalpA (Q11002) and Dm (X78555), schistosoma (P27730).

Figure 6:
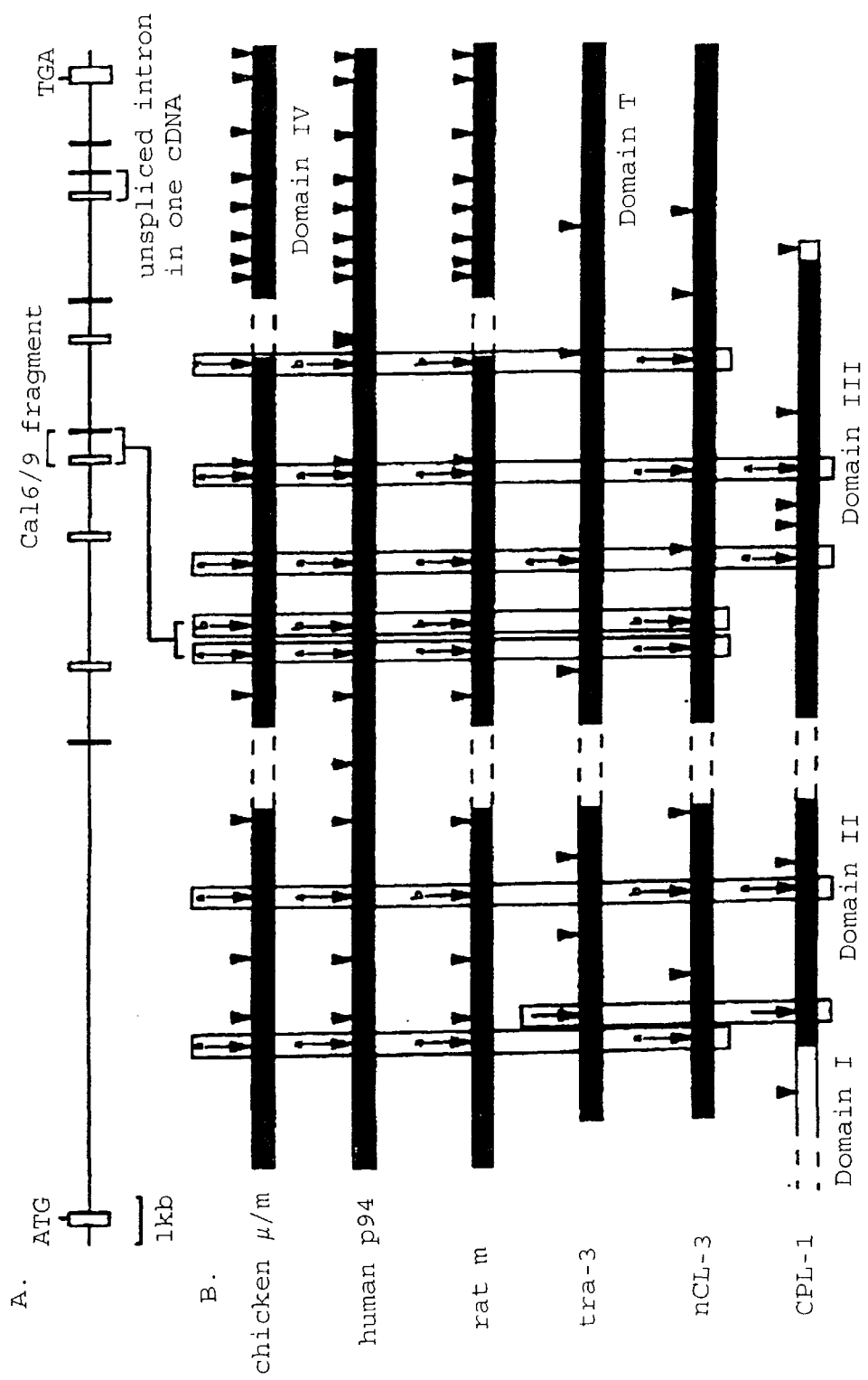
FIG. 6A shows the nCL-3 gene structure.
FIG. 6B shows the positions of various splicing sites of various calpains.

The nCL-3 gene structure is depicted in FIG. 6. The exon/intron splicing joins within the coding sequence of the gene were found by comparing the DNA sequences of genomic DNA and cDNA. Eleven introns were found within the coding sequence. The position of the splicing sites is marked by arrows in FIG. 4. The position of the genomic fragment which was amplified first with the primers Cal6 and Cal9 is marked by parentheses.

FIG. 6b shows the position of the splicing sites of various calpains. Surprisingly, nCL-3 and tra3 have, despite the relatively large degree of homology, no splice sites in common. The agreement in the position of some splice sites between nCL-3 and the vertebrate calpains indicates a common origin of the genes. The question mark over the last conserved splice site in the chicken μ/m-calpain gene indicates that the published sequence does not agree in the region of this splice site with the original cDNA sequence.

Besides the nCL-3 gene depicted in the sequence SEQ ID NO:1, a truncated form has been identified and is depicted in sequence SEQ ID NO:3. The derived amino acid sequence of the truncated nCL-3 gene is to be found in sequence SEQ ID NO:4. This truncated nCL-3 gene, which is designated nCL-3', presumably arises due to alternative splicing. Semiquantitative RT-PCR analyses with mRNA isolated from dE17 cells, using primers which cover the flanking regions of the intron (see FIG. 6), showed that the unspliced product accounts for about 0.5% of n-CL3 [sic] mRNA.

Figure 1:
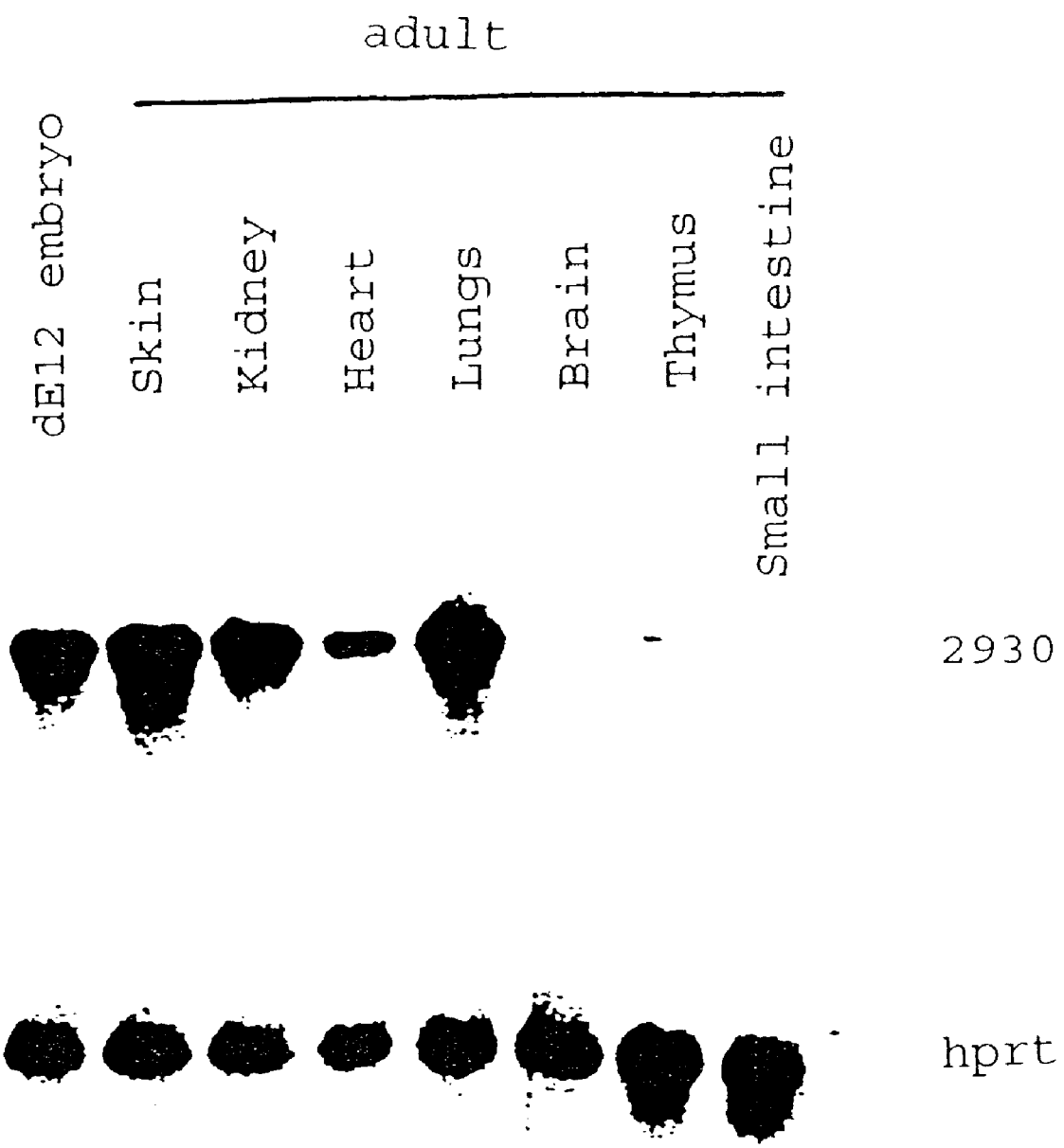
FIG. 1 shows mRNA analysis demonstrating that nCL-3 is expressed in the skin, kidney, heart, lung, thymus and liver.

The novel calpain nCL-3 according to the invention is expressed with varying intensity in many tissues (FIG. 1). In the mRNA analyses examined, it is clearly evident that nCL-3 is expressed in the skin, the kidney, the heart, the lung, the thymus and the liver.

The expression of the nCL-3 gene also varies in strength in humans. A low level of expression has been detected in all the tissues investigated. Strong expression was found in the colon, in the testes, in the kidney, in the liver and in the trachea.

The nCL-3 gene has been located on chromosome 7 in mice and chromosome 11 in humans. It is located on the long arm of the human chromosome at about 84 cM (=centi Morgen). This is a distance of 12–14 cM from the mapped position of μ-calpain (11q13). Mapping of nCL-3 very close to the glycoprotein A gene has been possible (11q13.5–q14).

The mouse ortholog nCL-3 gene has been located between 44 and 53 cM on mouse chromosome 7.

Methods of maximum specificity for inhibitor identification are required for identifying selective calpain inhibitors. It is important in this connection that the selected inhibitors inhibit only the required calpain(s) but not other cysteine proteases and thus intervene in physiological processes.

The test substances to be tested for their inhibitory activity can be, for example, chemical substances, microbial or plant extracts. Besides the test for their inhibitory activity on nCL-3, calpain I and/or II, they are normally tested for their activity on cathepsin B or other thiol proteases.

Good inhibitors should ideally display only slight or no activity on cathepsin B, L, elastase, papain, chymotrypsin or other cysteine proteases, but display good activity on calpains I and It is possible with the method according to the invention to identify by the novel calpain nCL-3 according to the invention inhibitors which are able to discriminate in their inhibitory effect between the various calpains calpain I, II, nCL-1, nCL-2 and/or nCL-3.

The various inhibitor tests were carried out as follows:
Cathepsin B Test

Cathepsin B inhibition was determined by a method similar to that of S. Hasnain et al., J. Biol. Chem. 1993, 268, 235–240.

2 μl of an inhibitor solution prepared from the chemical substance to be tested, a microbial or plant extract and DSMO [sic] (final concentration: 100 μM to 0.01 μM) are added to 88 μl of cathepsin B (from human liver supplied by Calbiochem, diluted to 5 units in 500 μM buffer). This mixture is preincubated at room temperature (=25° C.) for 60 minutes, and then the reaction is started by adding 10 μl of 10 mM Z-Arg-Arg-pNA (in buffer with 10% DMSO). The reaction is followed at 405 nm in a microtiter plate reader for minutes. The $IC_{50}$s are then determined from the maximum gradients.
Calpain I and II Test The activity of the calpain inhibitors was investigated in a colorimetric test using Hammarsten casein (Merck, Darmstadt) as substrate. The test was carried out in microtiter plates as published by Buroker-Kilgore and Wang in Anal. Biochem. 208, 1993, 387–392. The enzymes used were calpain I (0.04 U/test) from erythrocytes and calpain II (0.2 U/test) from kidneys, both from pigs, supplied by Calbiochem. The substances to be tested were incubated with the enzyme at room temperature for 60 minutes, the concentration of the solvent DMSO not exceeding 1%. After addition of the Bio-Rad color reagent, the optical density was measured at 595 nm in an SLT EAR 400 Easy Reader. The 50% enzyme activity is obtained from the optical densities determined at the maximum activity of the enzyme without inhibitors and the activity of the enzyme without addition of calcium.

The activity of calpain inhibitors can furthermore be determined using the substrate Suc-Leu Tyr-AMC [sic]. This fluorimetric method is described by Zhaozhao Li et al., J. Med. Chem. 36 (1993), 3472–3480.

Since calpains are intracellular cysteine proteases, calpain inhibitors must pass through the cell membrane in order to prevent degradation of intracellular proteins by calpain. Some known calpain inhibitors, such as E 64 and leupeptin, cross cell membranes only poorly and, accordingly, show only a poor effect on cells, although they are good calpain inhibitors. It is therefore advantageous to carry out an additional test for the ability of potential calpain inhibitors to cross membranes, such as the human platelet test.

Platelet test to determine the cellular activity of calpain inhibitors.

The calpain-mediated degradation of proteins in platelets was carried out as described by Zhaozhao Li et al., J. med. Chem. 36 (1993), 3472–3480. Human platelets were isolated from fresh sodium citrate blood from donors and adjusted to $10^7$ cells/ml in buffer (5 mM HEPES, 140 mM NaCl and 1 mg/ml BSA, pH 7.3).

Platelets (0.1 ml) are [sic] preincubated in 1 μl of various concentrations of potential inhibitors (dissolved in DMSO) for 5 minutes. This was followed by addition of the calcium ionophore A 23187 (1 μM in the test) and calcium (5 mM in the test) and further incubation at 37° C. for 5 minutes. After a centrifugation step, the platelets were taken up in SDS-PAGE sample buffer and boiled at 95° C. for 5 minutes, and the proteins were fractionated in an 8% gel. Degradation of the two proteins actin-binding protein (=ABP) and talin was followed by quantitative densitometry. After addition of calcium and ionophore, these proteins disappeared, and new bands with a molecular weight below 200 Kd were produced. The half-maximum enzyme activity is determined with or, as control, without inhibitor from this.

Also suitable for testing the ability to cross membranes are pieces of tissue such as brain sections or cell cultures.

The test for inhibition of nCL-3 is carried out in cells which express this protein, and the latter can be detected with a specific antibody. If cells are stimulated with, for example, calcium and the appropriate ionophore, this leads to activation of nCL-3. Takaomi Saido described in J. Biochem. 11 (1992), 81–86 the autolytic transition of μ-calpain after activation, and detection with antibodies. Corresponding antibodies are produced for detecting nCL-3. Calpain inhibitors prevent the autolytic transition, and corresponding quantification is possible with antibodies.

Besides the in vitro tests described, just as [sic] the cellular platelet test, all other calpain tests known to the skilled worker are suitable, such as the test for inhibition of glutamate-induced cell death in cortical neurons (Maulucci-Gedde M. A. et al., J. Neurosci. 7, 1987: 357–368), calcium-mediated cell death in NT2 cells (Squier M. K. T. et al., J. Cell. Physiol., 35 159, 1994: 229–237, Patel T. et al., Faseb Journal 590, 1996: 587–597) or analysis of tissue samples for degradation products of proteins such as spectrin, MAP2 or Tau (Ami Arai et al., Brain Research, 1991, 555, 276–280, James Brorson et al., Stroke, 1995, 26, 1259–1267).

For the in vitro test on nCL-3, the calpain nCL-3 or its animal or human homolog is purified from tissues or cells in which the enzyme is expressed, such as the kidney, the thymus, the liver, the lung, or from cells or microorganisms which contain at least one gene copy and/or a vector with at least one gene copy of the nCL-3 gene, and is used as crude extract or as pure enzyme.

For the methods according to the invention, the various calpain inhibitor tests are advantageously carried out in combination with the test for inhibition of nCL-3 enzyme activity by potential inhibitors. The inhibitors chosen for this inhibit either only the enzyme nCL-3 and not the other calpains or, conversely, only the other calpains and not the enzyme nCL-3 or the enzyme nCL-3 and at least one other calpain.

The various inhibitor tests are moreover carried out in such a way that, besides the test for the inhibitory effect of the test substance on nCL-3, calpain I and/or II, as a control the tests is [sic] carried out without the test substance. The inhibitory effects of the test substances can easily be detected by this test arrangement.

Another method according to the invention uses the enzyme nCL-3 for screening for new calpain inhibitors, it being possible for these inhibitors advantageously to inhibit all calpains in general or single calpains such as calpain I, II, nCL-1, nCL-2 or nCL-3. The various test substances can for this purpose be tested singly or in parallel in test systems. The test substances are advantageously screened for their inhibitory effect in parallel automated test systems.

In general, all substances are suitable for the inhibitor tests. Thus, the substances are derived, for example, from classical chemical synthesis, from combinatorial chemistry, from microbial, animal or plant extracts. Microbial extracts mean, for example, fermentation broths, disrupted microorganism cells or substances after biotransformation. Cell fractions are also suitable for the tests.

Suitable for cloning the nCL-3 gene or its animal homologs or its human homolog are all prokaryotic or eukaryotic expression systems suitable for isolating an enzymatically active gene product. Preferred expression systems are those allowing expression of the nCL-3 gene sequences in bacterial, fungal or animal cells, very particularly preferably in insect cells. Enzymatically active gene product means nCL-3 proteins which afford, immediately after isolation from the expressing organism, for example from a prokaryotic or eukaryotic cell, or after renaturation, an active protein which is able to cleave at least one known calpain substrate such as those mentioned above or itself by autocatalysis.

Suitable for determining the enzymatic activity are all calpain tests known to the skilled worker, such as in vitro tests like the tests for calpain I and II described above or cellular tests such as the platelet test. It is moreover possible to use as possibilities for detection tests based on a calorimetric assay (Buroker-Kilgore M. et al., Anal. Biochem. 208, 1993: 387–392) or based on a fluorescence assay.

In addition, enzymatically active gene product of nCL-3 also means all part-sequences which contain the catalytic center of the nCL-3 gene and/or other sequences of the nCL-3 gene and/or calpain gene sequences and/or other sequences and show enzymatic activity.

Host organisms mean all prokaryotic or eukaryotic organisms suitable as host organisms, are [sic] for example bacteria such as *Escherichia coli, Bacillus subtilis, Streptomyces lividans, Streptococcus carnosus*, yeasts such as *Saccharomyces cerevisiae, Schizosaccharomyces pombe*, fungi such as *Aspergillus niger*, insect cells such as *Spodoptera frugiperda*, Trichoplusia cells or all other insect cells suitable for viral expression, or animal cells such as CV1, COS, C127, 3T3 or CHO or human cells.

Expression systems mean the combination of the expression organisms mentioned above by way of example and the vectors suitable for the organisms, such as plasmids, viruses or phages, such as the T7 RNA polymerase/promoter system or vectors with regulatory sequences for phage λ.

The term expression systems preferably means the combination of *Escherichia coli* and its plasmids and phages or the baculovirus system and the appropriate insect cells such as Spodoptera frugiperda.

In addition, other 3' and/or 5' terminal regulatory sequences are suitable for advantageous expression according to the invention of the nCL-3 gene.

These regulatory sequences are intended to make specific expression of the nCL-3 gene possible. This may mean, for example, depending on the host organism that the gene is expressed or overexpressed only after induction, or that it is immediately expressed and/or overexpressed.

The regulatory sequences and factors may moreover preferably have a beneficial effect on, and thus increase, nCL-3 gene expression. Thus enhancement of the regulatory elements can advantageously take place at the level of transcription by using strong transcription signals such as promoters and/or enhancers. However, besides this, it is also possible to enhance translation by, for example, improving the stability of the mRNA.

Enhancers mean, for example, DNA sequences which bring about, via an improved interaction between RNA polymerase and DNA, an increase in nCL-3 gene expression.

One or more DNA sequences can be put upstream and/or downstream of the nCL-3 gene, with or without upstream promoter or with or without regulator gene, so that the gene is present in a gene structure.

Expression of the nCL-3 gene can furthermore be increased by increasing the copy number of the nCL-3 gene. To increase the copy number of the gene, the nCL-3 gene is, for example, amplified in a CHO expression vector. Also suitable as vectors are vectors of the pED series—dicistronic vectors—which also contain the amplifiable marker gene of dihydrofolate reductase. Details can be found in Current Protocols in Molecular Biology Vol. 2, 1994.

An increase in nCL-3 enzyme activity compared with the initial enzyme can be achieved, for example, by modifying the nCL-3 gene or its animal homologs by classical mutagenesis such as UV irradiation or treatment with chemical mutagents [sic] and/or by targeted mutagenesis such as site directed mutagenesis, deletion(s), insertion(s) and/or substitution(s). The enzyme activity can be increased, for example, by modifying the catalytic center in such a way that the substrate to be cleaved is converted more rapidly. Increased enzyme activity can also be achieved, besides the described gene amplification, by eliminating factors which repress enzyme biosynthesis and/or synthesizing active instead of inactive nCL-3 proteins. It is possible in this way to provide increased amounts of enzymes for the in vitro tests.

nCL-3 or its animal homologs can advantageously be cloned starting from genomic DNA or cDNA using, for example, the PCR technique (Molecular Cloning, Sambrok [sic], Fritsch and Maniatis, Cold Spring Harbor Laboratory Press, Second Edition 1989, Chapter 14, 1–35, ISBN 0-87969-309-6 and Saiki et al., Science, 239 (1988), 487ff), and nCL-3 can be cloned preferably using genomic DNA and particularly preferably using genomic DNA from mouse cells or human cells.

Suitable examples of a host organism for the cloning are all *Escherichia coli* strains, preferably the *Escherichia coli* strain DH10B. Vectors suitable for the cloning are all vectors suitable for expression in *Escherichia coli* (see Molecular Cloning, Sambrok [sic], Fritsch and Maniatis, Cold Spring Harbor Laboratory Press, Second Edition 1989, ISBN 0-87969-309-6). Particularly suitable examples are vectors derived from pBR or pUC or shuttle vectors, and pBluescript is very particularly suitable.

After isolation and sequencing, nCL-3 genes with nucleotide sequences which code for the amino acid sequence indicated in SEQ ID NO:2 or its allelic variantions [sic] are obtainable. Allelic variants mean nCL-3 variants which display 60–100% homology at the amino acid level, preferably 70–100%, very particularly preferably 80–100%. Allelic variants comprise in particular functional variants obtainable by deletion, insertion or substitution of nucleotides from the sequence depicted in SEQ ID NO:1 or SEQ ID NO:6, but where the nCL-3 activity is retained.

Analogs of nCL-3 mean, for example, animal homologs, truncated sequences such as nCL-3' (see SEQ ID NO:3), single-stranded DNA or RNA of the coding and noncoding DNA sequence, in particular antisense RNA.

Examples of derivatives of nCL-3 are those derivatives which can be cleaved enzymatically only with difficulty, if at all, such as the nucleic acid phosphonates or phosphothioates in which the phosphate group of the nucleic acids has been replaced by a phosphonate or thioate group respectively.

The promoter upstream of the indicated nucleotide sequence can also be modified by one or more nucleotide exchanges, by insertion(s), and/or deletion(s) but without impairing the functionality or effectiveness of the promoter. Furthermore, the promoter can also have its effectiveness increased by modifying its sequence or being completely replaced by more effective promoters also from heterologous organisms.

The calpain inhibitors identified by the methods according to the invention are suitable for producing medicines for treating diseases selected from the group of cardiovascular, immunological, inflammatory, allergic, neurological, neurodegenerative or oncological disorders such as restenosis, arthritis, ischemias of the heart, of the kidney or of the central nervous system (eg. stroke), inflammations, muscular dystrophies, cataracts of the eye (gray cataract), injuries to the central nervous system (eg. trauma), Alzheimer's disease, HIV-induced neuropathy, and Parkinson's and Huntigton's [sic] diseases.

The nCL-3 gene sequences according to the invention are also advantageously suitable for diagnosing diseases, for example diagnosing muscular dystrophy, or for gene therapy.

EXAMPLES

Example 1

Cloning of the nCL-3 Gene

Genomic DNA from ES E14 mouse cells was used for cloning the nCL-3 gene with the sequence SEQ ID NO:1. The 5'-3' (=forwards) and 3'-5' (=backwards) sequences of the primers CAL6 and CAL9 (see Table 1), and the following PCR conditions (see Molecular Cloning, Sambrok [sic], Fritsch and Maniatis, Cold Spring Harbor Laboratory Press, Second Edition 1989, Chapter 14, 1–35, ISBN 0-87969-309-6 and Saiki et al., Science 239 (1988), 487ff), were used for the cloning:

250 ng of forwards primer 250 ng of backwards primer 1.5 mM MgCl2 [sic]

0.2 mM dNTPS 50 mM KCl 10 mM Tris pH 9.0

1 μg of genomic DNA 2 units of Taq polymerase.

35 PCR cycles were carried out, keeping the temperature at 94° C. for 45 seconds, at 48° C. for 45 seconds and at 72° C. for 2 minutes.

The nCL-3 gene was cloned into the vector pBluescript (SK+) using the enzyme EcoRV (see Holten et al. Nucleic Acids Research, Vol. 19, No 5, 1156ff). The Escherichia coli strain DH10B was transformed with the pBluescript vector with the cloned-in nCL-3 gene as described by Maniatis et al. (see Molecular Cloning, Sambrok [sic], Fritsch and Maniatis, Cold Spring Harbor Laboratory Press, second edition 1989, volume 1, Chapter 1, 74–84 ISBN 0-87969-309-6 and Saiki et al., Science 239 (1988), 487ff).

It is also possible in this way to clone the human sequence of the nCL-3 gene with SEQ ID NO:6, it being possible to start from 0.1 ng of cDNA or 0.5 μg of genomic DNA. The cloning mixture may in addition advantageously contain 0.1% Triton X-100.

Example 2

Expression of the nCL-3 Gene in Various Mouse Tissues

For the expression, mRNA was isolated from dE12 embryos and from skin, kidney, heart, lung, brain, thymus and small intestinal tissue from mice. To extract the mRNA, the tissue was dispersed in liquid nitrogen and resuspended in 10 ml of a solution of 4 M guanidinium isothiocyanate, 25 mM Na citrate, 0.5% sarcosyl [sic] and 72 μl of 2-mercaptoethanol. Subsequently, 1 ml of Na acetate (pH 4.0), 10 ml of water-saturated phenol and 2 ml of chloroform were mixed in. The samples were centrifuged (5000×g, 4° C.) for minutes. The precipitate was discarded. The RNA was precipitated from the supernatant with one volume of isopropanol at −20° C. (precipitation for at least one hour) and again centrifuged for 30 minutes (19,000×g, 4° C.). The precipitate was resuspended in 300 μl and again precipitated with Na acetate/ethanol in the cold, and with 70% ethanol, centrifuged down (19,000×g, 4° C.), washed and dissolved in 300 μl of water. The mRNA concentration was then determined in a photometer at 250 nm and in an agarose gel with a 5 μl mRNA sample comparing with a reference.

Expression of the nCL-3 gene in the various mouse tissues was determined by RT-PCR, in which a cDNA copy was first produced using reverse transcriptase and starting from the isolated mRNA, with the aid of the following two primers:

a) forwards primer 5'-tagctcgagtggacgtaatcgtcgatgac-3' (SEQ ID NO:23)

b) backwards primer 5'-tagctcgagtgctgtaggctgtgcatacg-3' (SEQ ID NO:24) (see FIG. 1).

The cDNA was prepared in accordance with a GIBCO protocol as follows:

2 μl of oligo(dT) and 12 μl of DEPC dH$_2$O were added to 5 μg of mRNA (isolated by the method described above). This mixture was incubated at 70° C. for 10 minutes and then placed on ice. To the sample were added, in the stated sequence, 2 μl of 10×buffer, 2 μl of 25 mM MgCl$_2$, 1 μl of 10 mM dNTPs, 2 μl of 1 M DTT. After incubation at 23° C. for 5 minutes, 1 μl of Superscript reverse transcriptase was added, and the mixture was incubated further at 25° C. for 10 min, at 42° C. for 50 min and at 70° C. for 15 min. Then 1 μl of RNAse H and 79 μl of dH$_2$O were added and the reaction was continued in each case at 37° C. for 20 min and at 70° C. for 15 min. 1 μl of this cDNA was used for the RT-PCR reaction [sic].

The PCR reaction [sic] for detecting expression of nCL-3 was carried out as follows:

250 ng of forwards primer 250 ng of backwards primer 1.5 of MgCl2 [sic]

0.2 of dNTPS 50 of KCl 10 of Tris pH 9.0

1 μg of cDNa 2 units of Taq polymerase.

35 PCR cycles were carried out, keeping the temperature at 94° C. for 45 seconds, at 58° C. for 45 seconds and at 72 C for 1 minute.

It was shown in the tested tissues that nCL-3 is expressed in the dE12 embryos. nCL-3 is also expressed in the skin, the kidney, the heart, the lung and the thymus. Expression in the brain and in the small intestine is less than in the above-mentioned organs (not seen in FIG. 1). The internal standard used was hprt (=hypoxanthine phosphorus [sic] ribosyltransferase).

3rd Example

Cloning of the Human Sequence of nCL-3

The 3' end of the mouse or human nCL-3 cDNA was established by the RACE method (=rapid amplification of cDNA ends) as described by Frohman et al. (Proc. Natl. Acad. Sci. USA 85, 1988, 8998–9002) and Edwards et al. (Nucl. Acids Res. 19, 1991, 5227–5232). Human hippocampus Marathon-Ready cDNA (Clontech) was used for the human sequence of the 5' and 3' end. For the mouse sequence, cDNA from day 12 mouse embryos was used as described in Example 2. The human 3' end could not be isolated with the reverse primer in the kit. Cloning succeeded using a forwards primer complementary to the human EST sequence and a reverse primer corresponding to the last 6 amino acids of the mouse nCL-3 sequence (5'-tcagacagccgtgagagagg-3') (SEQ ID NO:22).

4th Example

Isolation and Characterization of Cosmid Clones

Cosmid clones with the mouse nCl-3 [sic] gene were isolated from a cosmid library produced from genomic ES mouse cell DNA by cloning in the vector pSuperCos (stratagene). The library had been divided into 348 pools each of 1000 clones. Positive pools were identified by PCR analysis using nCL-3-specific primers.

These pools were then plated out and and [sic] screened. Positive clones were identified by colony hybridization with $^{32}$P-labeled mouse nCL-3 cDNA fragments.

5th Example

RNA Expression Analysis

Expression of the human nCL-3 was investigated by hybridization of a human RNA master blot (Clontech) with a $^{32}$P-labeled human nCL-3 fragment (nucleotide 1–928 coding for amino acids 1–295). The hybridization and the highly stringent washing conditions were carried out in accordance with the manufacturer's instructions.

6th Example

Location of the nCL-3 Gene on the Chromosome

Location of the gene in the mouse took place by PCR analysis of genomic DNA which had been isolated from somatic mouse×hamster cell hybrids as had been described by Williamson et al. (Mamm. Genome 6, 1995, 429–432) using a set of DNAs disclosed by Schupp et al. (Immunogenet. 45, 1997, 180–187). The primer sequences used were 5'-tgcacagcctacagcataag-3' (SEQ ID NO:25) and 5'-tcagacagccgtgagagagg-3' (SEQ ID NO:22). It was possible with the aid of these primers to amplify an approximately 2.7 kb fragment of mouse and no hamster DNA. The PCR reactions were carried out using the expanded long template PCR system (Boehringer Mannheim) in accordance with the manufacturer's instructions at an annealing temperature of 58° C.

Location of the gene in humans took place using the NIGMS human/rodent somatic cell hybrid mapping panel (Coriell Cell Repositories). The following primers were used as primer sequences for the PCR reactions: 5'-acttcatcttctggcttcttgacttc-3' (SEQ ID NO:26) and 5'-gctgcatcaaccacaaggacac-3' (SEQ ID NO:27). The PCR amplification was carried out with an annealing temperature of 58° C. and resulted in a 600 bp fragment. The results were examined for agreement between the presence of human chromosomes and the PCR product. The exact location of the gene in the human chromosome was found using the Genebridge 4 RH panel (Research Genetics) and by transferring the PCR results to the location service of the MIF Center for Genome Research (http://www-genome.wi.mit.edu).

7th Example

Cathepsin B Test

The inhibition of cathepsin B was determined by methods similar to that of S. Hasnain et al., J. Biol. Chem. 168 (1993), 235–40. 2 μl of an inhibitor solution prepared from inhibitor and DMSO (final concentrations: 100 μM to 0.01 μM) are added to 88 μl of cathepsin B (cathepsin B from human liver (Calbiochem) diluted to 5 units in 500 μM buffer). This mixture is preincubated at room temperature (25° C.) for 60 minutes and then the reaction is started by adding 10 μl of 10 mM Z-Arg-Arg-pNA (in buffer with 10% DMSO). The reaction is followed at 405 nM [sic] in a microtiter plate reader for 30 minutes. The $IC_{50}$s are then determined from the maximum gradients.

8th Example

Calpain Test

The activity of the calpain inhibitors was investigated in a colorimetric test with Hammarsten casein (Merck, Darmstadt) as substrate. The test was carried out in a microtiter plate in accordance with the publication by Buroker-Kilgore and Wang in Anal. Biochemistry 208 (1993), 387–392. The enzyme used was 29/30, which had been expressed in one of the systems described above and then purified. The substances were incubated with the enzyme at room temperature for 60 minutes, the concentration of the solvent DMSO not exceeding 1%. After addition of the Bio-Rad color reagent, measurement of the optical density at 595 nm took place in an SLT EAR 400 Easy Reader. The 50% enzyme activity emerges from the optical densities determined at the maximum activity of the enzyme without inhibitors and the activity of the enzyme without addition of calcium.

9th Example

Platelet Test to Determine the Cellular Activity of Calpain Inhibitors

The calpain-mediated degradation of proteins in platelets was carried out as described by Zhaozhao Li et al., J. med. Chem. 36 (1993), 3472–3480. Human platelets were isolated from fresh sodium citrate blood from donors and adjusted to $10^7$ cells/ml in buffer (5 mM HEPES, 140 mM NaCl and 1 mg/ml BSA, pH 7.3).

Platelets (0.1 ml) are [sic] preincubated in 1 μl of various concentrations of inhibitors (dissolved in DMSO) for 5 minutes. This was followed by addition of the calcium ionophore A 23187 (1 μM in the test) and calcium (5 mM in the test) and further incubation at 37° C. for 5 minutes. After a centrifugation step, the platelets were taken up in SDS-PAGE sample buffer and boiled at 95° C. for 5 minutes, and the proteins were fractionated in an 8% gel. Degradation of the two proteins actin-binding protein (ABP) and talin was followed by quantitative densitometry, since after addition of calcium and ionophore, these proteins disappeared, and a new band with a molecular weight in the region of 200 kd was produced. The half-maximum enzyme activity is determined from this.

We claim:

1. An isolated DNA, which codes for an enzymatically active nCL-3 product, wherein the encoded amino acid sequence has a homology of from 80 to 100% with the amino acid sequence depicted in SEQ ID NO:2.

2. The DNA defined in claim 1, wherein the nucleic acid sequence is truncated, is as depicted in SEQ ID NO:3, and codes for an enzymatically active nCL-3 product.

3. The DNA defined in claim 1 having the sequence depicted in SEQ ID NO:6.

4. A gene construct comprising the DNA defined in claim 1 which is functionally linked to one or more regulatory signals to increase gene expression.

5. A process for preparing nCL-3, which process comprises the steps of cloning the DNA defined in claim 1 into a vector, and expressing the gene for nCL-3 in a host cell appropriate for the vector, and subsequently isolating the enzyme from the host cell.

6. The process defined in claim 5, wherein a vector which makes expression of the gene for nCL-3 possible in prokaryotic or eukaryotic cells is used.

7. The process defined in claim 5, wherein a bacterial, fungal or animal cell is used as host cell.

8. The process defined in claim 5, wherein baculoviruses are used as vector and insect cells are used as host cell.

9. An isolated DNA having the nucleotide sequence depicted in SEQ ID NO:1.

10. An isolated single stranded DNA or RNA, wherein the nucleic acid sequence is antisense to the coding sequence of the DNA defined in claim 1 and the single stranded DNA or RNA is able to anneal to the coding strand of the DNA defined in claim 1 under physiological conditions and is capable of inhibiting expression of the DNA defined in claim 1.

11. A derivative of the DNA defined in claim 1, wherein the phosphate group of the nucleic acids is replaced by a functional group selected from phosphonate and thioate groups.

12. An isolated single stranded RNA which codes for an enzymatically active nCL-3 product, wherein the encoded amino acid sequence has a homology of from 80 to 100% of the amino acid sequence depicted in SEQ ID NO:2.

* * * * *

```
                          SEQUENCE LISTING

<160> NUMBER OF SEQ ID NOS: 49

<210> SEQ ID NO 1
<211> LENGTH: 2459
<212> TYPE: DNA
<213> ORGANISM: Mus musculus
<220> FEATURE:
<221> NAME/KEY: CDS
<222> LOCATION: 194 . . 2116

<400> SEQUENCE: 1
ctgaagcccg ggggtccaag ttccaacccc cgcctgcggg ctgccggggt atcatctccc      60
cgcagagtcc cggccgtggc gcgggctggt ctagcctccg ctccagtgcc cgcactgtgc     120
tctgcatccc gggagtccag ctccagctgc ggcgacgcgg caggtgcctc cccttcttgg     180
ggacgtggtc acc atg ttc tcc tgc gcg aag gcc tat gag gac cag aac       229
            Met Phe Ser Cys Ala Lys Ala Tyr Glu Asp Gln Asn
              1               5                  10 tac tcg gcg ctg aag cgg gcc tgc ctg cgc aag aag gtg ctg ttc gag       277
Tyr Ser Ala Leu Lys Arg Ala Cys Leu Arg Lys Lys Val Leu Phe Glu
        15                  20                  25 gat ccc ctc ttc cct gcc acc gac gac tcc ctt tac tat aag ggc acc       325
Asp Pro Leu Phe Pro Ala Thr Asp Asp Ser Leu Tyr Tyr Lys Gly Thr
    30                  35                  40 cca ggg ccc aca gtc agg tgg aag cgg cct aag gat atc tgc gac gat       373
Pro Gly Pro Thr Val Arg Trp Lys Arg Pro Lys Asp Ile Cys Asp Asp
45                  50                  55                  60 ccc cgg ctc ttc gta gat ggc atc agc tcc cat gac ctg cac cag ggc       421
Pro Arg Leu Phe Val Asp Gly Ile Ser Ser His Asp Leu His Gln Gly
                65                  70                  75 cag gtg ggc aac tgc tgg ttt gtg gct gcc tgc tca tca ctg gcc tcc       469
```

```
Gln Val Gly Asn Cys Trp Phe Val Ala Ala Cys Ser Ser Leu Ala Ser
             80                  85                  90 cga gag tca ctc tgg cag aag gtc atc cca gac tgg aag gag cag gaa      517
Arg Glu Ser Leu Trp Gln Lys Val Ile Pro Asp Trp Lys Glu Gln Glu
         95                 100                 105 tgg aac ccc gag aag cct gac agc tat gct ggc atc ttc cac ttc aac      565
Trp Asn Pro Glu Lys Pro Asp Ser Tyr Ala Gly Ile Phe His Phe Asn
    110                 115                 120 ttc tgg cgc ttt ggg gag tgg gtg gac gta atc gtc gat gac cgg ctg      613
Phe Trp Arg Phe Gly Glu Trp Val Asp Val Ile Val Asp Asp Arg Leu
125                 130                 135                 140 ccc aca gtc aac aac cag ctc att tac tgc cat tcc aac tcc aaa aat      661
Pro Thr Val Asn Asn Gln Leu Ile Tyr Cys His Ser Asn Ser Lys Asn
                145                 150                 155 gag ttc tgg tgt gcc ctg gtg gag aag gcc tat gcc aag ctg gcc ggc      709
Glu Phe Trp Cys Ala Leu Val Glu Lys Ala Tyr Ala Lys Leu Ala Gly
            160                 165                 170 tgt tac cag gcc ctg gac gga ggc aac acg gcc gat gca ttg gtg gat      757
Cys Tyr Gln Ala Leu Asp Gly Gly Asn Thr Ala Asp Ala Leu Val Asp
        175                 180                 185 ttc aca ggt ggt gtt tct gaa ccc att gac ctg acc gag ggg gac ttg      805
Phe Thr Gly Gly Val Ser Glu Pro Ile Asp Leu Thr Glu Gly Asp Leu
    190                 195                 200 gcc act gac gag gct aag agg aat cag ctc ttt gag cga gtg ctg aag      853
Ala Thr Asp Glu Ala Lys Arg Asn Gln Leu Phe Glu Arg Val Leu Lys
205                 210                 215                 220 gtg cac agc aga ggc ggg ctc atc agt gcc tcc atc aag gct gtg aca      901
Val His Ser Arg Gly Gly Leu Ile Ser Ala Ser Ile Lys Ala Val Thr
                225                 230                 235 gca gct gac atg gag gcc cgc ctg gca tgt ggc ctg gtg aag ggc cat      949
Ala Ala Asp Met Glu Ala Arg Leu Ala Cys Gly Leu Val Lys Gly His
            240                 245                 250 gca tac gct gtc acc gat gtg cgc aag gtg cgc ctg ggc cat ggc ctg      997
Ala Tyr Ala Val Thr Asp Val Arg Lys Val Arg Leu Gly His Gly Leu
        255                 260                 265 ctg gcc ttc ttc aag tca gag aag ctt gat atg atc cgt ctg agg aac     1045
Leu Ala Phe Phe Lys Ser Glu Lys Leu Asp Met Ile Arg Leu Arg Asn
    270                 275                 280 ccc tgg ggc gag cgg gag tgg acg ggg ccc tgg agt gac acg tca gag     1093
Pro Trp Gly Glu Arg Glu Trp Thr Gly Pro Trp Ser Asp Thr Ser Glu
285                 290                 295                 300 gaa tgg cag aaa gtg agc aag agt gag agg gag aag atg ggc gtg acc     1141
Glu Trp Gln Lys Val Ser Lys Ser Glu Arg Glu Lys Met Gly Val Thr
                305                 310                 315 gtg cag gat gat ggg gaa ttc tgg atg acc ttt gag gac atg tgc cgg     1189
Val Gln Asp Asp Gly Glu Phe Trp Met Thr Phe Glu Asp Met Cys Arg
            320                 325                 330 tac ttt act gac atc att aaa tgc cgc ctg att aac acg tcc tac ctg     1237
Tyr Phe Thr Asp Ile Ile Lys Cys Arg Leu Ile Asn Thr Ser Tyr Leu
        335                 340                 345 agc atc cat aag aca tgg gag gag gcc cgg ctg cat ggt gcc tgg acg     1285
Ser Ile His Lys Thr Trp Glu Glu Ala Arg Leu His Gly Ala Trp Thr
    350                 355                 360 aga cat gag gac cca cag cag aac cgc agt gga ggc tgc atc aac cac     1333
Arg His Glu Asp Pro Gln Gln Asn Arg Ser Gly Gly Cys Ile Asn His
365                 370                 375                 380 aag gac act ttc ttc cag aac cca cag tac gta ttt gaa gtc aag aag     1381
Lys Asp Thr Phe Phe Gln Asn Pro Gln Tyr Val Phe Glu Val Lys Lys
                385                 390                 395
```

-continued

```
cca gaa gat gaa gtg ttg atc agt atc cag cag cgg ccg aag cgc tca    1429
Pro Glu Asp Glu Val Leu Ile Ser Ile Gln Gln Arg Pro Lys Arg Ser
            400                 405                 410 act cgc cgg gag ggc aaa ggc gag aat ctg gcc att ggc ttc gac atc    1477
Thr Arg Arg Glu Gly Lys Gly Glu Asn Leu Ala Ile Gly Phe Asp Ile
                415                 420                 425 tat aag gtg gaa gag aac cgc caa tac cgt atg cac agc cta cag cat    1525
Tyr Lys Val Glu Glu Asn Arg Gln Tyr Arg Met His Ser Leu Gln His
    430                 435                 440 aag gcc gcc agc tcc atc tac atc aat tcc cgc agc gtt ttt ttg agg    1573
Lys Ala Ala Ser Ser Ile Tyr Ile Asn Ser Arg Ser Val Phe Leu Arg
445                 450                 455                 460 aca gag ctg ccc gag ggc cgc tac gtt atc atc cct acc acc ttt gag    1621
Thr Glu Leu Pro Glu Gly Arg Tyr Val Ile Ile Pro Thr Thr Phe Glu
                465                 470                 475 cca ggc cac act ggc gag ttc ctg ctc cga gtc ttc aca gat gtc ccc    1669
Pro Gly His Thr Gly Glu Phe Leu Leu Arg Val Phe Thr Asp Val Pro
                480                 485                 490 tcc aac tgc cgg gaa cta cgc ctg gat gag ccc cct cgg acc tgt tgg    1717
Ser Asn Cys Arg Glu Leu Arg Leu Asp Glu Pro Pro Arg Thr Cys Trp
            495                 500                 505 agt tcc ctc tgt ggc tac cct cag cag gtg gcc cag gta cat gtc ctg    1765
Ser Ser Leu Cys Gly Tyr Pro Gln Gln Val Ala Gln Val His Val Leu
510                 515                 520 ggg gct gct ggc ctc aag gac tcc cca aca gga gca aac tca tat gtg    1813
Gly Ala Ala Gly Leu Lys Asp Ser Pro Thr Gly Ala Asn Ser Tyr Val
525                 530                 535                 540 atc atc aag tgt gag ggc gaa aag gtt cgc tca gct gtg cag aga ggg    1861
Ile Ile Lys Cys Glu Gly Glu Lys Val Arg Ser Ala Val Gln Arg Gly
                545                 550                 555 acc tcg aca cca gag tac aat gta aaa ggc atc ttc tat cgc aag aag    1909
Thr Ser Thr Pro Glu Tyr Asn Val Lys Gly Ile Phe Tyr Arg Lys Lys
                560                 565                 570 ctg gct cag cct atc acc gtg cag gtt tgg aat cac cga gtc ctg aag    1957
Leu Ala Gln Pro Ile Thr Val Gln Val Trp Asn His Arg Val Leu Lys
        575                 580                 585 gat gaa ttc ctg ggc cag gtg cac ctg aag act gcc ccg gat gac ctg    2005
Asp Glu Phe Leu Gly Gln Val His Leu Lys Thr Ala Pro Asp Asp Leu
    590                 595                 600 cag gac ctc cac acc ctc cat ctc cag gac cgc agt agc cgg cag ccc    2053
Gln Asp Leu His Thr Leu His Leu Gln Asp Arg Ser Ser Arg Gln Pro
605                 610                 615                 620 agt gac ctg cca ggc att gta gct gtg cga gtc ctc tgc agt gcc tct    2101
Ser Asp Leu Pro Gly Ile Val Ala Val Arg Val Leu Cys Ser Ala Ser
                625                 630                 635 ctc acg gct gtc tgaccccagc ctgcctgtcc tgccccacta gtcctcacca        2153
Leu Thr Ala Val
            640 ctactcgcat gtccccacct tgcctgggac cagcctggga accagacact ggggcccttt   2213 cctcactctt ccactgaccc actgtgtgac ctgaagagag ccctgccctc tctgagcctc    2273 agtgtttgga gggccccaaa gaattcccgt cttgtggggg agttttcttg cctaagattt    2333 aatgcagttc tctctaccca gtgggcgctg ctgttaaggg gccatctgct gaaaacgttt    2393 ccccaggccc tgctgtctgc caggagtgcc aagtgtcaac tgtttacaca caaactgcca    2453 tgtccc                                                              2459

<210> SEQ ID NO 2
<211> LENGTH: 640
```

```
<212> TYPE: PRT
<213> ORGANISM: Mus musculus

<400> SEQUENCE: 2

Met Phe Ser Cys Ala Lys Ala Tyr Glu Asp Gln Asn Tyr Ser Ala Leu
 1               5                  10                  15

Lys Arg Ala Cys Leu Arg Lys Lys Val Leu Phe Glu Asp Pro Leu Phe
                20                  25                  30

Pro Ala Thr Asp Asp Ser Leu Tyr Tyr Lys Gly Thr Pro Gly Pro Thr
            35                  40                  45

Val Arg Trp Lys Arg Pro Lys Asp Ile Cys Asp Asp Pro Arg Leu Phe
50                  55                  60

Val Asp Gly Ile Ser Ser His Asp Leu His Gln Gly Gln Val Gly Asn
65                  70                  75                  80

Cys Trp Phe Val Ala Ala Cys Ser Ser Leu Ala Ser Arg Glu Ser Leu
                85                  90                  95

Trp Gln Lys Val Ile Pro Asp Trp Lys Glu Gln Glu Trp Asn Pro Glu
                100                 105                 110

Lys Pro Asp Ser Tyr Ala Gly Ile Phe His Phe Asn Phe Trp Arg Phe
            115                 120                 125

Gly Glu Trp Val Asp Val Ile Val Asp Asp Arg Leu Pro Thr Val Asn
130                 135                 140

Asn Gln Leu Ile Tyr Cys His Ser Asn Ser Lys Asn Glu Phe Trp Cys
145                 150                 155                 160

Ala Leu Val Glu Lys Ala Tyr Ala Lys Leu Ala Gly Cys Tyr Gln Ala
                165                 170                 175

Leu Asp Gly Gly Asn Thr Ala Asp Ala Leu Val Asp Phe Thr Gly Gly
            180                 185                 190

Val Ser Glu Pro Ile Asp Leu Thr Glu Gly Asp Leu Ala Thr Asp Glu
            195                 200                 205

Ala Lys Arg Asn Gln Leu Phe Glu Arg Val Leu Lys Val His Ser Arg
210                 215                 220

Gly Gly Leu Ile Ser Ala Ser Ile Lys Ala Val Thr Ala Ala Asp Met
225                 230                 235                 240

Glu Ala Arg Leu Ala Cys Gly Leu Val Lys Gly His Ala Tyr Ala Val
                245                 250                 255

Thr Asp Val Arg Lys Val Arg Leu Gly His Gly Leu Leu Ala Phe Phe
            260                 265                 270

Lys Ser Glu Lys Leu Asp Met Ile Arg Leu Arg Asn Pro Trp Gly Glu
            275                 280                 285

Arg Glu Trp Thr Gly Pro Trp Ser Asp Thr Ser Glu Glu Trp Gln Lys
290                 295                 300

Val Ser Lys Ser Glu Arg Glu Lys Met Gly Val Thr Val Gln Asp Asp
305                 310                 315                 320

Gly Glu Phe Trp Met Thr Phe Glu Asp Met Cys Arg Tyr Phe Thr Asp
                325                 330                 335

Ile Ile Lys Cys Arg Leu Ile Asn Thr Ser Tyr Leu Ser Ile His Lys
            340                 345                 350

Thr Trp Glu Glu Ala Arg Leu His Gly Ala Trp Thr Arg His Glu Asp
            355                 360                 365

Pro Gln Gln Asn Arg Ser Gly Gly Cys Ile Asn His Lys Asp Thr Phe
            370                 375                 380

Phe Gln Asn Pro Gln Tyr Val Phe Glu Val Lys Lys Pro Glu Asp Glu
385                 390                 395                 400
```

```
Val Leu Ile Ser Ile Gln Gln Arg Pro Lys Arg Ser Thr Arg Arg Glu
            405                 410                 415

Gly Lys Gly Glu Asn Leu Ala Ile Gly Phe Asp Ile Tyr Lys Val Glu
        420                 425                 430

Glu Asn Arg Gln Tyr Arg Met His Ser Leu Gln His Lys Ala Ala Ser
        435                 440                 445

Ser Ile Tyr Ile Asn Ser Arg Ser Val Phe Leu Arg Thr Glu Leu Pro
        450                 455                 460

Glu Gly Arg Tyr Val Ile Ile Pro Thr Thr Phe Glu Pro Gly His Thr
465                 470                 475                 480

Gly Glu Phe Leu Leu Arg Val Phe Thr Asp Val Pro Ser Asn Cys Arg
            485                 490                 495

Glu Leu Arg Leu Asp Glu Pro Pro Arg Thr Cys Trp Ser Ser Leu Cys
            500                 505                 510

Gly Tyr Pro Gln Gln Val Ala Gln Val His Val Leu Gly Ala Ala Gly
            515                 520                 525

Leu Lys Asp Ser Pro Thr Gly Ala Asn Ser Tyr Val Ile Ile Lys Cys
530                 535                 540

Glu Gly Glu Lys Val Arg Ser Ala Val Gln Arg Gly Thr Ser Thr Pro
545                 550                 555                 560

Glu Tyr Asn Val Lys Gly Ile Phe Tyr Arg Lys Leu Ala Gln Pro
            565                 570                 575

Ile Thr Val Gln Val Trp Asn His Arg Val Leu Lys Asp Glu Phe Leu
            580                 585                 590

Gly Gln Val His Leu Lys Thr Ala Pro Asp Asp Leu Gln Asp Leu His
            595                 600                 605

Thr Leu His Leu Gln Asp Arg Ser Ser Arg Gln Pro Ser Asp Leu Pro
        610                 615                 620

Gly Ile Val Ala Val Arg Val Leu Cys Ser Ala Ser Leu Thr Ala Val
625                 630                 635                 640

<210> SEQ ID NO 3
<211> LENGTH: 1743
<212> TYPE: DNA
<213> ORGANISM: Mus musculus balb/c
<220> FEATURE:
<221> NAME/KEY: CDS
<222> LOCATION: 194 .. 1735

<400> SEQUENCE: 3
ctgaagcccg ggggtccaag ttccaacccc cgcctgcggg ctgccggggt atcatctccc      60
cgcagagtcc cggccgtggc gcgggctggt ctagcctccg ctccagtgcc cgcactgtgc     120
tctgcatccc gggagtccag ctccagctgc ggcgacgcgg caggtgcctc cccttcttgg     180
ggacgtggtc acc atg ttc tcc tgc gcg aag gcc tat gag gac cag aac       229
            Met Phe Ser Cys Ala Lys Ala Tyr Glu Asp Gln Asn
              1               5                  10 tac tcg gcg ctg aag cgg gcc tgc ctg cgc aag aag gtg ctg ttc gag      277
Tyr Ser Ala Leu Lys Arg Ala Cys Leu Arg Lys Lys Val Leu Phe Glu
        15                  20                  25 gat ccc ctc ttc cct gcc acc gac gac tcc ctt tac tat aag ggc acc      325
Asp Pro Leu Phe Pro Ala Thr Asp Asp Ser Leu Tyr Tyr Lys Gly Thr
    30                  35                  40 cca ggg ccc aca gtc agg tgg aag cgg cct aag gat atc tgc gac gat      373
Pro Gly Pro Thr Val Arg Trp Lys Arg Pro Lys Asp Ile Cys Asp Asp
45                  50                  55                  60
```

-continued

| | |
|---|---|
| ccc cgg ctc ttc gta gat ggc atc agc tcc cat gac ctg cac cag ggc<br>Pro Arg Leu Phe Val Asp Gly Ile Ser Ser His Asp Leu His Gln Gly<br>                  65                      70                  75 | 421 |
| cag gtg ggc aac tgc tgg ttt gtg gct gcc tgc tca tca ctg gcc tcc<br>Gln Val Gly Asn Cys Trp Phe Val Ala Ala Cys Ser Ser Leu Ala Ser<br>        80                      85                      90 | 469 |
| cga gag tca ctc tgg cag aag gtc atc cca gac tgg aag gag cag gaa<br>Arg Glu Ser Leu Trp Gln Lys Val Ile Pro Asp Trp Lys Glu Gln Glu<br>           95                    100                105 | 517 |
| tgg aac ccc gag aag cct gac agc tat gct ggc atc ttc cac ttc aac<br>Trp Asn Pro Glu Lys Pro Asp Ser Tyr Ala Gly Ile Phe His Phe Asn<br>110                    115                    120 | 565 |
| ttc tgg cgc ttt ggg gag tgg gtg gac gta atc gtc gat gac cgg ctg<br>Phe Trp Arg Phe Gly Glu Trp Val Asp Val Ile Val Asp Asp Arg Leu<br>125                    130                    135                140 | 613 |
| ccc aca gtc aac aac cag ctc att tac tgc cat tcc aac tcc aaa aat<br>Pro Thr Val Asn Asn Gln Leu Ile Tyr Cys His Ser Asn Ser Lys Asn<br>                  145                    150                155 | 661 |
| gag ttc tgg tgt gcc ctg gtg gag aag gcc tat gcc aag ctg gcc ggc<br>Glu Phe Trp Cys Ala Leu Val Glu Lys Ala Tyr Ala Lys Leu Ala Gly<br>                    160                    165                170 | 709 |
| tgt tac cag gcc ctg gac gga ggc aac acg gcc gat gca ttg gtg gat<br>Cys Tyr Gln Ala Leu Asp Gly Gly Asn Thr Ala Asp Ala Leu Val Asp<br>175                    180                    185 | 757 |
| ttc aca ggt ggt gtt tct gaa ccc att gac ctg acc gag ggg gac ttg<br>Phe Thr Gly Gly Val Ser Glu Pro Ile Asp Leu Thr Glu Gly Asp Leu<br>        190                      195                    200 | 805 |
| gcc act gac gag gct aag agg aat cag ctc ttt gag cga gtg ctg aag<br>Ala Thr Asp Glu Ala Lys Arg Asn Gln Leu Phe Glu Arg Val Leu Lys<br>205                    210                    215                220 | 853 |
| gtg cac agc aga ggc ggg ctc atc agt gcc tcc atc aag gct gtg aca<br>Val His Ser Arg Gly Gly Leu Ile Ser Ala Ser Ile Lys Ala Val Thr<br>                  225                    230                235 | 901 |
| gca gct gac atg gag gcc cgc ctg gca tgt ggc ctg gtg aag ggc cat<br>Ala Ala Asp Met Glu Ala Arg Leu Ala Cys Gly Leu Val Lys Gly His<br>                    240                    245                250 | 949 |
| gca tac gct gtc acc gat gtg cgc aag gtg cgc ctg ggc cat ggc ctg<br>Ala Tyr Ala Val Thr Asp Val Arg Lys Val Arg Leu Gly His Gly Leu<br>        255                      260                    265 | 997 |
| ctg gcc ttc ttc aag tca gag aag ctt gat atg atc cgt ctg agg aac<br>Leu Ala Phe Phe Lys Ser Glu Lys Leu Asp Met Ile Arg Leu Arg Asn<br>270                    275                    280 | 1045 |
| ccc tgg ggc gag cgg gag tgg acg ggg ccc tgg agt gac acg tca gag<br>Pro Trp Gly Glu Arg Glu Trp Thr Gly Pro Trp Ser Asp Thr Ser Glu<br>285                    290                    295                300 | 1093 |
| gaa tgg cag aaa gtg agc aag agt gag agg gag aag atg ggc gtg acc<br>Glu Trp Gln Lys Val Ser Lys Ser Glu Arg Glu Lys Met Gly Val Thr<br>                  305                    310                315 | 1141 |
| gtg cag gat gat ggg gaa ttc tgg atg acc ttt gag gac atg tgc cgg<br>Val Gln Asp Asp Gly Glu Phe Trp Met Thr Phe Glu Asp Met Cys Arg<br>                    320                    325                330 | 1189 |
| tac ttt act gac atc att aaa tgc cgc ctg att aac acg tcc tac ctg<br>Tyr Phe Thr Asp Ile Ile Lys Cys Arg Leu Ile Asn Thr Ser Tyr Leu<br>        335                      340                    345 | 1237 |
| agc atc cat aag aca tgg gag gag gcc cgg ctg cat ggt gcc tgg acg<br>Ser Ile His Lys Thr Trp Glu Glu Ala Arg Leu His Gly Ala Trp Thr<br>350                    355                    360 | 1285 |
| aga cat gag gac cca cag cag aac cgc agt gga ggc tgc atc aac cac<br>Arg His Glu Asp Pro Gln Gln Asn Arg Ser Gly Gly Cys Ile Asn His<br>365                    370                    375                380 | 1333 |

```
aag gac act ttc ttc cag aac cca cag tac gta ttt gaa gtc aag aag      1381
Lys Asp Thr Phe Phe Gln Asn Pro Gln Tyr Val Phe Glu Val Lys Lys
            385                 390                 395 cca gaa gat gaa gtg ttg atc agt atc cag cag cgg ccg aag cgc tca      1429
Pro Glu Asp Glu Val Leu Ile Ser Ile Gln Gln Arg Pro Lys Arg Ser
        400                 405                 410 act cgc cgg gag ggc aaa ggc gag aat ctg gcc att ggc ttc gac atc      1477
Thr Arg Arg Glu Gly Lys Gly Glu Asn Leu Ala Ile Gly Phe Asp Ile
                415                 420                 425 tat aag gtg gaa gag aac cgc caa tac cgt atg cac agc cta cag cat      1525
Tyr Lys Val Glu Glu Asn Arg Gln Tyr Arg Met His Ser Leu Gln His
    430                 435                 440 aag gcc gcc agc tcc atc tac atc aat tcc cgc agc gtt ttt ttg agg      1573
Lys Ala Ala Ser Ser Ile Tyr Ile Asn Ser Arg Ser Val Phe Leu Arg
445                 450                 455                 460 aca gag ctg ccc gag ggc cgc tac gtt atc atc cct acc acc ttt gag      1621
Thr Glu Leu Pro Glu Gly Arg Tyr Val Ile Ile Pro Thr Thr Phe Glu
                465                 470                 475 cca ggc cac act ggc gag ttc ctg ctc cga gtc ttc aca gat gtc ccc      1669
Pro Gly His Thr Gly Glu Phe Leu Leu Arg Val Phe Thr Asp Val Pro
        480                 485                 490 tcc aac tgc cgg tgt gtg ggg gct agg gct agt gac cgc atg cat ata      1717
Ser Asn Cys Arg Cys Val Gly Ala Arg Ala Ser Asp Arg Met His Ile
                495                 500                 505 tac ccc atg ctg ggc tagatttaa c                                      1743
Tyr Pro Met Leu Gly
    510

<210> SEQ ID NO 4
<211> LENGTH: 513
<212> TYPE: PRT
<213> ORGANISM: Mus musculus balb/c

<400> SEQUENCE: 4

Met Phe Ser Cys Ala Lys Ala Tyr Glu Asp Gln Asn Tyr Ser Ala Leu
 1               5                  10                  15

Lys Arg Ala Cys Leu Arg Lys Lys Val Leu Phe Glu Asp Pro Leu Phe
                20                  25                  30

Pro Ala Thr Asp Asp Ser Leu Tyr Tyr Lys Gly Thr Pro Gly Pro Thr
            35                  40                  45

Val Arg Trp Lys Arg Pro Lys Asp Ile Cys Asp Asp Pro Arg Leu Phe
        50                  55                  60

Val Asp Gly Ile Ser Ser His Asp Leu His Gln Gly Gln Val Gly Asn
 65                  70                  75                  80

Cys Trp Phe Val Ala Ala Cys Ser Ser Leu Ala Ser Arg Glu Ser Leu
                85                  90                  95

Trp Gln Lys Val Ile Pro Asp Trp Lys Glu Gln Glu Trp Asn Pro Glu
            100                 105                 110

Lys Pro Asp Ser Tyr Ala Gly Ile Phe His Phe Asn Phe Trp Arg Phe
        115                 120                 125

Gly Glu Trp Val Asp Val Ile Val Asp Asp Arg Leu Pro Thr Val Asn
    130                 135                 140

Asn Gln Leu Ile Tyr Cys His Ser Asn Ser Lys Asn Glu Phe Trp Cys
145                 150                 155                 160

Ala Leu Val Glu Lys Ala Tyr Ala Lys Leu Ala Gly Cys Tyr Gln Ala
                165                 170                 175

Leu Asp Gly Gly Asn Thr Ala Asp Ala Leu Val Asp Phe Thr Gly Gly
```

```
                    180             185             190
Val Ser Glu Pro Ile Asp Leu Thr Glu Gly Asp Leu Ala Thr Asp Glu
        195             200             205

Ala Lys Arg Asn Gln Leu Phe Glu Arg Val Leu Lys Val His Ser Arg
210             215             220

Gly Gly Leu Ile Ser Ala Ser Ile Lys Ala Val Thr Ala Ala Asp Met
225             230             235             240

Glu Ala Arg Leu Ala Cys Gly Leu Val Lys Gly His Ala Tyr Ala Val
            245             250             255

Thr Asp Val Arg Lys Val Arg Leu Gly His Gly Leu Leu Ala Phe Phe
            260             265             270

Lys Ser Glu Lys Leu Asp Met Ile Arg Leu Arg Asn Pro Trp Gly Glu
        275             280             285

Arg Glu Trp Thr Gly Pro Trp Ser Asp Thr Ser Glu Glu Trp Gln Lys
    290             295             300

Val Ser Lys Ser Glu Arg Glu Lys Met Gly Val Thr Val Gln Asp Asp
305             310             315             320

Gly Glu Phe Trp Met Thr Phe Glu Asp Met Cys Arg Tyr Phe Thr Asp
                325             330             335

Ile Ile Lys Cys Arg Leu Ile Asn Thr Ser Tyr Leu Ser Ile His Lys
            340             345             350

Thr Trp Glu Glu Ala Arg Leu His Gly Ala Trp Thr Arg His Glu Asp
        355             360             365

Pro Gln Gln Asn Arg Ser Gly Gly Cys Ile Asn His Lys Asp Thr Phe
    370             375             380

Phe Gln Asn Pro Gln Tyr Val Phe Glu Val Lys Lys Pro Glu Asp Glu
385             390             395             400

Val Leu Ile Ser Ile Gln Gln Arg Pro Lys Arg Ser Thr Arg Arg Glu
                405             410             415

Gly Lys Gly Glu Asn Leu Ala Ile Gly Phe Asp Ile Tyr Lys Val Glu
            420             425             430

Glu Asn Arg Gln Tyr Arg Met His Ser Leu Gln His Lys Ala Ala Ser
        435             440             445

Ser Ile Tyr Ile Asn Ser Arg Ser Val Phe Leu Arg Thr Glu Leu Pro
    450             455             460

Glu Gly Arg Tyr Val Ile Ile Pro Thr Thr Phe Glu Pro Gly His Thr
465             470             475             480

Gly Glu Phe Leu Leu Arg Val Phe Thr Asp Val Pro Ser Asn Cys Arg
                485             490             495

Cys Val Gly Ala Arg Ala Ser Asp Arg Met His Ile Tyr Pro Met Leu
            500             505             510

Gly

<210> SEQ ID NO 5
<211> LENGTH: 504
<212> TYPE: DNA
<213> ORGANISM: Mus musculus ES E14
<220> FEATURE:
<221> NAME/KEY: exon
<222> LOCATION: 1 . . 33
<220> FEATURE:
<221> NAME/KEY: intron
<222> LOCATION: 34 . .440
<220> FEATURE:
<221> NAME/KEY: exon
<222> LOCATION: 441 . . 504
```

-continued

```
<400> SEQUENCE: 5
cgagcgggag tggacgggcc cctggagtga cacgtgaggc tcaccagggt tgggctggg        60 tatgggcaca gaggcaagga caagcggtga cactggactg ggccttgcag ggtctgggag       120
agatgctctg aggaaaaaat gggagactta ctttccagtg taagtgtggt gcttggggg       180 taggttcatc aaggacagtg gccagaagtg tggcatgctt tgtacgtgga caatggcgcc      240
tcaccagctt tattccctga cttcatagcc ttagcataaa ggaagatcac agttcctagt      300
gggagagaac agaggcttct tagcagggct gggcatggcc tccaggtctc tacccacagt      360
gctctgcagg cggcttggtc cagagctctc ccttgggcca ctcctcttat cccgttccct      420
ccctgatact cactccccag gtcagaggaa tggcagaaag tgagcaagag tgagagggag      480
aagatgggcg tgaccgtgca ggat                                             504

<210> SEQ ID NO 6
<211> LENGTH: 1975
<212> TYPE: DNA
<213> ORGANISM: Homo sapiens
<220> FEATURE:
<221> NAME/KEY: CDS
<222> LOCATION: 44 .. 1963

<400> SEQUENCE: 6
actcactata gggctcgagc ggccgcccgg gcaggtagcc acc atg ttc tcg tgt         55
                                             Met Phe Ser Cys
                                              1 gtg aag ccc tat gag gac cag aac tac tca gcc ctg agg cgg gac tgc        103
Val Lys Pro Tyr Glu Asp Gln Asn Tyr Ser Ala Leu Arg Arg Asp Cys
  5                  10                  15                  20 cgg cgc agg aag gtg ctc ttc gag gac ccc ctc ttc ccc gcc act gac        151
Arg Arg Arg Lys Val Leu Phe Glu Asp Pro Leu Phe Pro Ala Thr Asp
                 25                  30                  35 gac tca ctc tac tat aag ggc acg ccg ggg ccc gcc gtc agg cgg aag        199
Asp Ser Leu Tyr Tyr Lys Gly Thr Pro Gly Pro Ala Val Arg Arg Lys
             40                  45                  50 cga ccc aag ggc atc tgc gag gac ccc cgc ctc ttt gtg gat ggc atc        247
Arg Pro Lys Gly Ile Cys Glu Asp Pro Arg Leu Phe Val Asp Gly Ile
         55                  60                  65 agc tcc cac gac ctg cac cag ggc cag gtg ggc aac tgc tgg ttt gtg        295
Ser Ser His Asp Leu His Gln Gly Gln Val Gly Asn Cys Trp Phe Val
     70                  75                  80 gca gcc tgc tcg tca ctt gcc tcc cgg gag tcg ctg tgg caa aag gtc        343
Ala Ala Cys Ser Ser Leu Ala Ser Arg Glu Ser Leu Trp Gln Lys Val
 85                  90                  95                 100 atc cca gac tgg aag gag cag gaa tgg gac ccc gaa aag ccc aac gcc        391
Ile Pro Asp Trp Lys Glu Gln Glu Trp Asp Pro Glu Lys Pro Asn Ala
                105                 110                 115 tac gcg ggc atc ttc cac ttc cac ttc tgg cgc ttc ggg gaa tgg gtg        439
Tyr Ala Gly Ile Phe His Phe His Phe Trp Arg Phe Gly Glu Trp Val
            120                 125                 130 gac gtg gtc atc gat gac cgg ctg ccc aca gtc aac aac cag ctc atc        487
Asp Val Val Ile Asp Asp Arg Leu Pro Thr Val Asn Asn Gln Leu Ile
        135                 140                 145 tac tgc cac tcc aac tcc cgc aat gag ttt tgg tgc gcc cta gtg gag        535
Tyr Cys His Ser Asn Ser Arg Asn Glu Phe Trp Cys Ala Leu Val Glu
    150                 155                 160 aag gcc tat gcc aaa ctg gca ggc tgt tac cag gcc ctg gat gga ggc        583
Lys Ala Tyr Ala Lys Leu Ala Gly Cys Tyr Gln Ala Leu Asp Gly Gly
165                 170                 175                 180
```

-continued

| | |
|---|---|
| aac aca gca gac gca ctg gtg gac ttc acg ggt ggt gtt tct gag ccc<br>Asn Thr Ala Asp Ala Leu Val Asp Phe Thr Gly Gly Val Ser Glu Pro<br>                            185                            190                        195 | 631 |
| atc gac ctg acc gag ggt gac ttt gcc aac gat gag act aag agg aac<br>Ile Asp Leu Thr Glu Gly Asp Phe Ala Asn Asp Glu Thr Lys Arg Asn<br>                 200                            205                        210 | 679 |
| cag ctc ttt gag cgc atg tta aag gtg cac agc cgg ggc ggc ctc atc<br>Gln Leu Phe Glu Arg Met Leu Lys Val His Ser Arg Gly Gly Leu Ile<br>               215                            220                        225 | 727 |
| agt gcc tcc atc aag gca gtg aca gca gct gac atg gag gcc cgc ctg<br>Ser Ala Ser Ile Lys Ala Val Thr Ala Ala Asp Met Glu Ala Arg Leu<br>230                          235                            240 | 775 |
| gcg tgc ggc ctg gta aag ggc cac gca tac gcc gtc act gat gtg cgc<br>Ala Cys Gly Leu Val Lys Gly His Ala Tyr Ala Val Thr Asp Val Arg<br>245                          250                          255                        260 | 823 |
| aag gtg cgc ctg ggc cac ggc cta ctg gcc ttc ttc aag tca gag aag<br>Lys Val Arg Leu Gly His Gly Leu Leu Ala Phe Phe Lys Ser Glu Lys<br>               265                            270                        275 | 871 |
| ttg gac atg atc cgc ctg cgc aac ccc tgg ggc gag cgg gag tgg aac<br>Leu Asp Met Ile Arg Leu Arg Asn Pro Trp Gly Glu Arg Glu Trp Asn<br>                 280                            285                        290 | 919 |
| ggg ccc tgg agt gac acc tcg gag gag tgg cag aaa gtg agc aag agt<br>Gly Pro Trp Ser Asp Thr Ser Glu Glu Trp Gln Lys Val Ser Lys Ser<br>               295                            300                        305 | 967 |
| gag cgg gag aag atg ggt gtg acc gtg cag gac gac ggt gag ttc tgg<br>Glu Arg Glu Lys Met Gly Val Thr Val Gln Asp Asp Gly Glu Phe Trp<br>310                          315                            320 | 1015 |
| atg acc ttc gag gac gtg tgc cgg tac ttc acg gac atc atc aag tgc<br>Met Thr Phe Glu Asp Val Cys Arg Tyr Phe Thr Asp Ile Ile Lys Cys<br>325                          330                          335                        340 | 1063 |
| cgc gtg atc aac aca tcc cac ctg agc atc cac aag acg tgg gag gag<br>Arg Val Ile Asn Thr Ser His Leu Ser Ile His Lys Thr Trp Glu Glu<br>               345                            350                        355 | 1111 |
| gcc cgg ctg cat ggc gcc tgg acg ctg cat gag gac ccg cga cag aac<br>Ala Arg Leu His Gly Ala Trp Thr Leu His Glu Asp Pro Arg Gln Asn<br>                 360                            365                        370 | 1159 |
| cgc ggt ggc ggc tgc atc aac cac aag gac acc ttc ttc cag aac cca<br>Arg Gly Gly Gly Cys Ile Asn His Lys Asp Thr Phe Phe Gln Asn Pro<br>                            375                            380                        385 | 1207 |
| cag tac atc ttc gaa gtc aag aag cca gaa gat gaa gtc ctg atc tgt<br>Gln Tyr Ile Phe Glu Val Lys Lys Pro Glu Asp Glu Val Leu Ile Cys<br>390                          395                          400 | 1255 |
| atc cag cag cgg cca aag cgg tct acg cgc cgg gag ggc aag ggt gag<br>Ile Gln Gln Arg Pro Lys Arg Ser Thr Arg Arg Glu Gly Lys Gly Glu<br>405                          410                          415                        420 | 1303 |
| aac ctg gcc att ggc ttt gac atc tac aag gtg gag gag aac cgc cag<br>Asn Leu Ala Ile Gly Phe Asp Ile Tyr Lys Val Glu Glu Asn Arg Gln<br>                            425                            430                        435 | 1351 |
| tac cgc atg cac agc ctg cag cac aag gcc gcc agc tcc atc tac atc<br>Tyr Arg Met His Ser Leu Gln His Lys Ala Ala Ser Ser Ile Tyr Ile<br>                 440                            445                        450 | 1399 |
| aac tca cgc agc gtc ttc ctg cgc acc gac cag ccc gag ggc cgc tat<br>Asn Ser Arg Ser Val Phe Leu Arg Thr Asp Gln Pro Glu Gly Arg Tyr<br>               455                            460                        465 | 1447 |
| gtc atc atc ccc aca acc ttc gag cca ggc cac act ggc gag ttc ctg<br>Val Ile Ile Pro Thr Thr Phe Glu Pro Gly His Thr Gly Glu Phe Leu<br>               470                            475                        480 | 1495 |
| ctc cga gtc ttc act gat gtg ccc tcc aac tgc cgg gag ctg cgc ctg<br>Leu Arg Val Phe Thr Asp Val Pro Ser Asn Cys Arg Glu Leu Arg Leu<br>485                          490                          495                        500 | 1543 |

```
gat gag ccc cca cac acc tgc tgg agc tcc ctc tgt ggc tac ccc cag      1591
Asp Glu Pro Pro His Thr Cys Trp Ser Ser Leu Cys Gly Tyr Pro Gln
            505                 510                 515 ctg gtg acc cag gta cat gtc ctg gga gct gct ggc ctc aag gac tcc      1639
Leu Val Thr Gln Val His Val Leu Gly Ala Ala Gly Leu Lys Asp Ser
            520                 525                 530 cca aca ggg gct aac tct tat gtg atc atc aag tgt gag gga gac aaa      1687
Pro Thr Gly Ala Asn Ser Tyr Val Ile Ile Lys Cys Glu Gly Asp Lys
            535                 540                 545 gtc cgc tcg gct gtg cag aag ggc acc tcc aca cca gag tac aat gtg      1735
Val Arg Ser Ala Val Gln Lys Gly Thr Ser Thr Pro Glu Tyr Asn Val
        550                 555                 560 aaa ggc atc ttc tac cgc aag aag ctg agc cag ccc atc act gta cag      1783
Lys Gly Ile Phe Tyr Arg Lys Lys Leu Ser Gln Pro Ile Thr Val Gln
565                 570                 575                 580 gtc tgg aac cac cga gtg ctg aag gat gaa ttt ctg ggc cag gtg cac      1831
Val Trp Asn His Arg Val Leu Lys Asp Glu Phe Leu Gly Gln Val His
                585                 590                 595 cta aag gct gac ccg gac aac ctc cag gcc ctg cat acc ctc cac ctc      1879
Leu Lys Ala Asp Pro Asp Asn Leu Gln Ala Leu His Thr Leu His Leu
            600                 605                 610 cgg gac cga aat agc cgg cag ccc agc aac ctg cca ggc act gtg gcc      1927
Arg Asp Arg Asn Ser Arg Gln Pro Ser Asn Leu Pro Gly Thr Val Ala
            615                 620                 625 gtg cac att ctc agc agc acc tct ctc acg gct gtc tgactcgagc           1973
Val His Ile Leu Ser Ser Thr Ser Leu Thr Ala Val
            630                 635                 640 ta                                                                    1975

<210> SEQ ID NO 7
<211> LENGTH: 640
<212> TYPE: PRT
<213> ORGANISM: Homo sapiens

<400> SEQUENCE: 7

Met Phe Ser Cys Val Lys Pro Tyr Glu Asp Gln Asn Tyr Ser Ala Leu
 1               5                  10                  15

Arg Arg Asp Cys Arg Arg Arg Lys Val Leu Phe Glu Asp Pro Leu Phe
            20                  25                  30

Pro Ala Thr Asp Asp Ser Leu Tyr Tyr Lys Gly Thr Pro Gly Pro Ala
        35                  40                  45

Val Arg Arg Lys Arg Pro Lys Gly Ile Cys Glu Asp Pro Arg Leu Phe
    50                  55                  60

Val Asp Gly Ile Ser Ser His Asp Leu His Gln Gly Gln Val Gly Asn
65                  70                  75                  80

Cys Trp Phe Val Ala Ala Cys Ser Ser Leu Ala Ser Arg Glu Ser Leu
                85                  90                  95

Trp Gln Lys Val Ile Pro Asp Trp Lys Glu Gln Glu Trp Asp Pro Glu
            100                 105                 110

Lys Pro Asn Ala Tyr Ala Gly Ile Phe His Phe His Phe Trp Arg Phe
        115                 120                 125

Gly Glu Trp Val Asp Val Val Ile Asp Asp Arg Leu Pro Thr Val Asn
    130                 135                 140

Asn Gln Leu Ile Tyr Cys His Ser Asn Ser Arg Asn Glu Phe Trp Cys
145                 150                 155                 160

Ala Leu Val Glu Lys Ala Tyr Ala Lys Leu Ala Gly Cys Tyr Gln Ala
                165                 170                 175
```

-continued

```
Leu Asp Gly Gly Asn Thr Ala Asp Ala Leu Val Asp Phe Thr Gly Gly
            180                 185                 190
Val Ser Glu Pro Ile Asp Leu Thr Glu Gly Asp Phe Ala Asn Asp Glu
        195                 200                 205
Thr Lys Arg Asn Gln Leu Phe Glu Arg Met Leu Lys Val His Ser Arg
    210                 215                 220
Gly Gly Leu Ile Ser Ala Ser Ile Lys Ala Val Thr Ala Ala Asp Met
225                 230                 235                 240
Glu Ala Arg Leu Ala Cys Gly Leu Val Lys Gly His Ala Tyr Ala Val
                245                 250                 255
Thr Asp Val Arg Lys Val Arg Leu Gly His Gly Leu Leu Ala Phe Phe
            260                 265                 270
Lys Ser Glu Lys Leu Asp Met Ile Arg Leu Arg Asn Pro Trp Gly Glu
        275                 280                 285
Arg Glu Trp Asn Gly Pro Trp Ser Asp Thr Ser Glu Glu Trp Gln Lys
    290                 295                 300
Val Ser Lys Ser Glu Arg Glu Lys Met Gly Val Thr Val Gln Asp Asp
305                 310                 315                 320
Gly Glu Phe Trp Met Thr Phe Glu Asp Val Cys Arg Tyr Phe Thr Asp
                325                 330                 335
Ile Ile Lys Cys Arg Val Ile Asn Thr Ser His Leu Ser Ile His Lys
            340                 345                 350
Thr Trp Glu Glu Ala Arg Leu His Gly Ala Trp Thr Leu His Glu Asp
        355                 360                 365
Pro Arg Gln Asn Arg Gly Gly Gly Cys Ile Asn His Lys Asp Thr Phe
    370                 375                 380
Phe Gln Asn Pro Gln Tyr Ile Phe Glu Val Lys Lys Pro Glu Asp Glu
385                 390                 395                 400
Val Leu Ile Cys Ile Gln Gln Arg Pro Lys Arg Ser Thr Arg Arg Glu
                405                 410                 415
Gly Lys Gly Glu Asn Leu Ala Ile Gly Phe Asp Ile Tyr Lys Val Glu
            420                 425                 430
Glu Asn Arg Gln Tyr Arg Met His Ser Leu Gln His Lys Ala Ala Ser
        435                 440                 445
Ser Ile Tyr Ile Asn Ser Arg Ser Val Phe Leu Arg Thr Asp Gln Pro
    450                 455                 460
Glu Gly Arg Tyr Val Ile Pro Thr Thr Phe Glu Pro Gly His Thr
465                 470                 475                 480
Gly Glu Phe Leu Leu Arg Val Phe Thr Asp Val Pro Ser Asn Cys Arg
                485                 490                 495
Glu Leu Arg Leu Asp Glu Pro Pro His Thr Cys Trp Ser Ser Leu Cys
            500                 505                 510
Gly Tyr Pro Gln Leu Val Thr Gln Val His Val Leu Gly Ala Ala Gly
        515                 520                 525
Leu Lys Asp Ser Pro Thr Gly Ala Asn Ser Tyr Val Ile Ile Lys Cys
    530                 535                 540
Glu Gly Asp Lys Val Arg Ser Ala Val Gln Lys Gly Thr Ser Thr Pro
545                 550                 555                 560
Glu Tyr Asn Val Lys Gly Ile Phe Tyr Arg Lys Leu Ser Gln Pro
                565                 570                 575
Ile Thr Val Gln Val Trp Asn His Arg Val Leu Lys Asp Glu Phe Leu
            580                 585                 590
```

Gly Gln Val His Leu Lys Ala Asp Pro Asp Asn Leu Gln Ala Leu His
            595                 600                 605

Thr Leu His Leu Arg Asp Arg Asn Ser Arg Gln Pro Ser Asn Leu Pro
            610                 615                 620

Gly Thr Val Ala Val His Ile Leu Ser Ser Thr Ser Leu Thr Ala Val
625                 630                 635                 640

<210> SEQ ID NO 8
<211> LENGTH: 19
<212> TYPE: DNA
<213> ORGANISM: Artificial Sequence
<220> FEATURE:
<223> OTHER INFORMATION: PCR primer
<220> FEATURE:
<221> NAME/KEY: misc_feature
<222> LOCATION: 2, 5, 17
<223> OTHER INFORMATION: residues 2, 5, 17 may be any nucleic acid

<400> SEQUENCE: 8 tngngaytg ytggytnyt                                            19

<210> SEQ ID NO 9
<211> LENGTH: 20
<212> TYPE: DNA
<213> ORGANISM: Artificial Sequence
<220> FEATURE:
<223> OTHER INFORMATION: PCR primer
<220> FEATURE:
<221> NAME/KEY: misc_feature
<222> LOCATION: 3, 12, 18
<223> OTHER INFORMATION: residues 3, 12, 18 may be any nucleic acid

<400> SEQUENCE: 9
ytngaraarg cntaygcnaa                                          20

<210> SEQ ID NO 10
<211> LENGTH: 20
<212> TYPE: DNA
<213> ORGANISM: Artificial Sequence
<220> FEATURE:
<223> OTHER INFORMATION: PCR primer
<220> FEATURE:
<221> NAME/KEY: misc_feature
<222> LOCATION: 4, 10, 19
<223> OTHER INFORMATION: residues 4, 10, 19 may be any nucleic acid

<400> SEQUENCE: 10
yttngcrtan gcyttytcna                                          20

<210> SEQ ID NO 11
<211> LENGTH: 20
<212> TYPE: DNA
<213> ORGANISM: Artificial Sequence
<220> FEATURE:
<223> OTHER INFORMATION: PCR primer
<220> FEATURE:
<221> NAME/KEY: misc_feature
<222> LOCATION: 3, 9, 15
<223> OTHER INFORMATION: residues 3, 9, 15 may be any nucleic acid

<400> SEQUENCE: 11
gtnaarggnc aygcntaywc                                          20

<210> SEQ ID NO 12
<211> LENGTH: 20
<212> TYPE: DNA
<213> ORGANISM: Artificial Sequence
<220> FEATURE:

```
<223> OTHER INFORMATION: PCR primer
<220> FEATURE:
<221> NAME/KEY: misc_feature
<222> LOCATION: 6, 12, 18
<223> OTHER INFORMATION: residues 6, 12, 18 may be any nucleic acid

<400> SEQUENCE: 12
gwrtangcrt gnccyttnac                                               20

<210> SEQ ID NO 13
<211> LENGTH: 17
<212> TYPE: DNA
<213> ORGANISM: Artificial Sequence
<220> FEATURE:
<223> OTHER INFORMATION: PCR primer
<220> FEATURE:
<221> NAME/KEY: misc_feature
<222> LOCATION: 3, 6, 12
<223> OTHER INFORMATION: residues 3, 6, 12 may be any nucleic acid

<400> SEQUENCE: 13
ytncgnaayc cntgggg                                                  17

<210> SEQ ID NO 14
<211> LENGTH: 20
<212> TYPE: DNA
<213> ORGANISM: Artificial Sequence
<220> FEATURE:
<223> OTHER INFORMATION: PCR primer
<220> FEATURE:
<221> NAME/KEY: misc_feature
<222> LOCATION: 6, 12, 15, 18
<223> OTHER INFORMATION: residues 6, 12, 15, 18 may be any nucleic acid

<400> SEQUENCE: 14
ccccanggrt tncgnarncg                                               20

<210> SEQ ID NO 15
<211> LENGTH: 18
<212> TYPE: DNA
<213> ORGANISM: Artificial Sequence
<220> FEATURE:
<223> OTHER INFORMATION: PCR primer
<220> FEATURE:
<221> NAME/KEY: misc_feature
<222> LOCATION: 6
<223> OTHER INFORMATION: residues 6 may be any nucleic acid

<400> SEQUENCE: 15
gayggngart tytggatg                                                 18

<210> SEQ ID NO 16
<211> LENGTH: 20
<212> TYPE: DNA
<213> ORGANISM: Artificial Sequence
<220> FEATURE:
<223> OTHER INFORMATION: PCR primer
<220> FEATURE:
<221> NAME/KEY: misc_feature
<222> LOCATION: 15
<223> OTHER INFORMATION: residues 15 may be any nucleic acid

<400> SEQUENCE: 16
swcatccara aytcnccrtc                                               20

<210> SEQ ID NO 17
<211> LENGTH: 17
<212> TYPE: DNA
<213> ORGANISM: Artificial Sequence
```

-continued

```
<220> FEATURE:
<223> OTHER INFORMATION: PCR primer
<220> FEATURE:
<221> NAME/KEY: misc_feature
<222> LOCATION: 1, 16
<223> OTHER INFORMATION: residues 1 and 16 may be any nucleic acid

<400> SEQUENCE: 17
narrttrcaw atytcna                                                      17

<210> SEQ ID NO 18
<211> LENGTH: 12
<212> TYPE: PRT
<213> ORGANISM: Mus musculus

<400> SEQUENCE: 18

Gln Gly Gln Val Gly Asn Cys Trp Phe Val Ala Ala
1               5                   10

<210> SEQ ID NO 19
<211> LENGTH: 828
<212> TYPE: PRT
<213> ORGANISM: Drosophila melanogaster

<400> SEQUENCE: 19

Met Asp Asp Leu Arg Gly Phe Leu Arg Gln Ala Gly Gln Glu Phe Leu
1               5                   10                  15

Asn Ala Ala Gly Glu Ala Ala Met Gly Ala Ala Lys Asp Val Val Gly
                20                  25                  30

Ser Val Ile Asn Glu Ile Phe Ile Lys Lys Glu Ala Asp Thr Lys Arg
            35                  40                  45

Val Leu Pro Ser Ile Lys Asn Met Arg Val Leu Gly Glu Lys Ser Ser
        50                  55                  60

Ser Leu Gly Pro Tyr Ser Glu Val Gln Asp Tyr Glu Thr Ile Leu Asn
65                  70                  75                  80

Ser Cys Leu Ala Ser Gly Ser Leu Phe Glu Asp Pro Leu Phe Pro Ala
                85                  90                  95

Ser Asn Glu Ser Leu Gln Phe Ser Arg Arg Pro Asp Arg His Ile Glu
            100                 105                 110

Trp Leu Arg Pro His Glu Ile Ala Glu Asn Pro Gln Phe Phe Val Glu
        115                 120                 125

Gly Tyr Ser Arg Phe Asp Val Gln Gln Gly Glu Leu Gly Asp Cys Trp
    130                 135                 140

Leu Leu Ala Ala Thr Ala Asn Leu Thr Gln Glu Ser Asn Leu Phe Phe
145                 150                 155                 160

Arg Val Ile Pro Ala Glu Gln Ser Phe Glu Glu Asn Tyr Ala Gly Ile
                165                 170                 175

Phe His Phe Arg Phe Trp Gln Tyr Gly Lys Trp Val Asp Val Ile Ile
            180                 185                 190

Asp Asp Arg Leu Pro Thr Tyr Asn Gly Glu Leu Met Tyr Met His Ser
        195                 200                 205

Thr Glu Lys Asn Glu Phe Trp Ser Ala Leu Leu Glu Lys Ala Tyr Ala
    210                 215                 220

Lys Leu His Gly Ser Tyr Glu Ala Leu Lys Gly Gly Ser Thr Cys Glu
225                 230                 235                 240

Ala Met Glu Asp Phe Thr Gly Gly Val Ser Glu Trp Tyr Asp Leu Lys
                245                 250                 255

Glu Ala Pro Gly Asn Leu Phe Thr Ile Leu Gln Lys Ala Ala Glu Arg
```

```
                    260                 265                 270
Asn Ser Met Met Gly Cys Ser Ile Glu Pro Asp Pro Asn Val Thr Glu
                275                 280                 285

Ala Glu Thr Pro Gln Gly Leu Ile Arg Gly His Ala Tyr Ser Ile Thr
290                 295                 300

Lys Val Cys Leu Ile Asp Ile Val Thr Pro Asn Arg Gln Gly Lys Ile
305                 310                 315                 320

Pro Met Ile Arg Met Arg Asn Pro Trp Gly Asn Glu Ala Glu Trp Asn
                325                 330                 335

Gly Pro Trp Ser Asp Ser Ser Pro Glu Trp Arg Tyr Ile Pro Glu Glu
                340                 345                 350

Gln Lys Ala Glu Ile Gly Leu Thr Phe Asp Arg Asp Gly Glu Phe Trp
                355                 360                 365

Met Ser Phe Gln Asp Phe Leu Asn His Phe Asp Arg Val Glu Ile Cys
        370                 375                 380

Asn Leu Ser Pro Asp Ser Leu Thr Glu Asp Gln Gln Asn Ser Gly Lys
385                 390                 395                 400

Arg Lys Trp Glu Met Ser Met Tyr Glu Gly Glu Trp Thr Pro Gly Val
                405                 410                 415

Thr Ala Gly Gly Cys Arg Asn Phe Leu Asp Thr Phe Trp His Asn Pro
                420                 425                 430

Gln Tyr Ile Ile Thr Leu Val Asp Pro Asp Glu Glu Asp Glu Glu Gly
                435                 440                 445

Gln Cys Thr Val Ile Val Ala Leu Met Gln Lys Asn Arg Arg Ser Lys
        450                 455                 460

Arg Asn Met Gly Met Glu Cys Leu Thr Ile Gly Phe Ala Ile Tyr Ser
465                 470                 475                 480

Leu Asn Asp Arg Glu Leu Glu Asn Arg Pro Gln Gly Leu Asn Phe Phe
                485                 490                 495

Arg Tyr Lys Ser Ser Val Gly Arg Ser Pro His Phe Ile Asn Thr Arg
                500                 505                 510

Glu Val Cys Ala Arg Phe Lys Leu Pro Pro Gly His Tyr Leu Ile Val
                515                 520                 525

Pro Ser Thr Phe Asp Pro Asn Glu Glu Gly Glu Phe Ile Ile Arg Val
530                 535                 540

Phe Ser Glu Thr Gln Asn Asn Met Glu Glu Asn Asp Asp His Val Gly
545                 550                 555                 560

Tyr Gly Gly Lys Ala Asp Thr Ile Thr Pro Gly Phe Pro Thr Pro Lys
                565                 570                 575

Pro Ile Asp Pro Gln Lys Glu Gly Leu Arg Arg Leu Phe Asp Ser Ile
                580                 585                 590

Ala Gly Lys Asp Met Glu Val Asp Trp Met Glu Leu Lys Arg Ile Leu
                595                 600                 605

Asp His Ser Met Arg Asp Asp Leu Pro Lys Pro Val Val Phe Asn Arg
                610                 615                 620

Phe Ser Asn Asn Met Ala Phe Glu Thr Gln Ala Ala Gly Pro Gly Asp
625                 630                 635                 640

Asp Gly Ala Gly Ala Cys Gly Leu Leu Ser Leu Ile Cys Gly Pro Phe
                645                 650                 655

Leu Lys Gly Thr Pro Phe Glu Glu Gln Leu Gly Met Asn Asp Gln Ser
                660                 665                 670

Asn Lys Arg Leu Ile Gly Asp Asn Pro Ala Asp Gly Gly Pro Val Thr
                675                 680                 685
```

```
Ala Asn Ala Ile Val Asp Glu Thr His Gly Phe Ser Lys Asp Val Cys
        690                 695                 700

Arg Ser Met Val Ala Met Leu Asp Ala Asp Lys Ser Gly Lys Leu Gly
705                 710                 715                 720

Phe Glu Glu Phe Glu Thr Leu Leu Ser Glu Ile Ala Lys Trp Lys Ala
                725                 730                 735

Ile Phe Lys Val Tyr Asp Val Glu Asn Thr Gly Arg Val Ser Gly Phe
            740                 745                 750

Gln Leu Arg Glu Ala Leu Asn Ser Ala Gly Tyr His Leu Asn Asn Arg
        755                 760                 765

Val Leu Asn Val Leu Gly His Arg Tyr Gly Ser Arg Asp Gly Lys Ile
770                 775                 780

Ala Phe Asp Asp Phe Ile Met Cys Ala Val Lys Ile Lys Thr Tyr Ile
785                 790                 795                 800

Asp Ile Phe Lys Glu Arg Asp Thr Glu Lys Asn Glu Thr Ala Thr Phe
                805                 810                 815

Thr Leu Glu Glu Trp Ile Glu Arg Thr Ile Tyr Ser
                820                 825

<210> SEQ ID NO 20
<211> LENGTH: 648
<212> TYPE: PRT
<213> ORGANISM: Caenorhabditis elegans

<400> SEQUENCE: 20

Met Thr Arg Ser Glu Lys Thr Arg His Phe Gly Asn Gln Asn Tyr Glu
1               5                   10                  15

Lys Leu Arg Lys Ile Cys Ile Lys Lys Gln Pro Phe Val Asp Thr
            20                  25                  30

Leu Phe Pro Pro Thr Asn Gln Ser Leu Phe Leu Glu Gln Arg Gln Ser
        35                  40                  45

Ser Asp Ile Val Trp Lys Arg Pro Gly Glu Leu His Pro Asp Pro His
    50                  55                  60

Leu Phe Val Glu Gly Ala Ser Pro Asn Asp Val Thr Gln Gly Ile Leu
65                  70                  75                  80

Gly Asn Cys Trp Phe Val Ser Ala Cys Ser Ala Leu Thr His Asn Phe
                85                  90                  95

Lys Leu Leu Ala Gln Val Ile Pro Asp Ala Asp Asp Gln Glu Trp Ser
            100                 105                 110

Thr Lys His Ala Tyr Ala Gly Ile Phe Arg Phe Arg Phe Trp Arg Phe
        115                 120                 125

Gly Lys Trp Val Glu Val Val Ile Asp Asp Leu Leu Pro Thr Arg Asp
    130                 135                 140

Gly Lys Leu Leu Phe Ala Arg Ser Lys Thr Pro Asn Glu Phe Trp Ser
145                 150                 155                 160

Ala Leu Leu Glu Lys Ala Phe Ala Lys Leu Tyr Gly Cys Tyr Glu Asn
                165                 170                 175

Leu Val Gly Gly His Leu Ser Asp Ala Leu Gln Asp Val Ser Gly Gly
            180                 185                 190

Val Ala Glu Thr Leu His Val Arg Lys Phe Leu Lys Asp Asp Pro Asn
        195                 200                 205

Asp Thr Glu Leu Lys Leu Phe Asn Asp Leu Lys Thr Ala Phe Asp Lys
    210                 215                 220

Gly Ala Leu Val Val Ala Ala Ile Ala Ala Arg Thr Lys Glu Glu Ile
```

```
            225                 230                 235                 240

Glu Glu Ser Leu Asp Cys Gly Leu Val Lys Gly His Ala Tyr Ala Val
                        245                 250                 255

Ser Ala Val Cys Thr Ile Asp Val Thr Asn Pro Asn Glu Arg Ser Phe
                        260                 265                 270

Thr Ser Phe Ile Met Gly Ser Lys Arg Lys Gln Asn Leu Ile Arg Leu
                        275                 280                 285

Gln Asn Pro Trp Gly Lys Glu Trp Asn Gly Ala Trp Ser Asp Asp
                290                 295                 300

Ser Pro Glu Trp Gln Asn Val Ser Ala Ser Gln Leu Ser Thr Met Gly
        305                 310                 315                 320

Val Gln Pro Ala Asn Ser Asp Ser Asp Asp Gly Asp Phe Trp Met Pro
                        325                 330                 335

Trp Glu Ser Phe Val His Tyr Phe Thr Asp Ile Ser Leu Cys Gln Leu
                        340                 345                 350

Phe Asn Thr Ser Val Phe Ser Phe Ser Arg Ser Tyr Asp Glu Gln Ile
                        355                 360                 365

Val Phe Ser Glu Trp Thr Thr Asn Gly Lys Lys Ser Gly Ala Pro Asp
                370                 375                 380

Asp Arg Ala Gly Gly Cys His Asn Phe Lys Ala Thr Phe Cys Asn Asn
        385                 390                 395                 400

Pro Gln Tyr Ile Phe Asp Ile Pro Ser Pro Asn Cys Ser Val Met Phe
                        405                 410                 415

Ala Leu Ile Gln Asn Asp Pro Ser Glu Gly Leu Lys Lys Arg Glu Pro
                        420                 425                 430

Phe Val Thr Ile Gly Met His Val Met Lys Val Glu Asn Asn Arg Gln
                        435                 440                 445

Tyr Arg Val His Thr Ala Met His Pro Ile Ala Ile Ser Asp Tyr Ala
                        450                 455                 460

Ser Gly Arg Ser Val Tyr Leu His Leu Gln Ser Leu Pro Arg Gly Arg
        465                 470                 475                 480

Tyr Leu Leu Ile Pro Thr Thr Phe Ala Pro Lys Glu Gln Thr Leu Phe
                        485                 490                 495

Met Leu Arg Val Tyr Ser Asp Glu His Ile His Phe Ser Pro Leu Thr
                        500                 505                 510

Lys His Ala Pro Lys Leu Gly Leu Leu Lys Cys Lys Ser Ala Gln Ser
                        515                 520                 525

Val Thr Arg Leu Thr Ile His Gly Val Asp Phe Asn Ser Ala Ser Thr
        530                 535                 540

Gly Thr His Asn Val Tyr Ala Ile Leu Lys Asp Ser Arg Lys Ser Phe
        545                 550                 555                 560

Arg Thr Lys Thr Leu Ser Gly Val Lys Ser Ile Gln Trp Asp Glu Gln
                        565                 570                 575

Phe Leu Phe His Lys Ser Lys Asn Arg Gln Gln Tyr Lys Ile Glu Val
                        580                 585                 590

Trp Glu Asp Arg Lys Met Ala Arg Asp His Leu Leu Ala Gln Ser Val
                        595                 600                 605

Ile Ile Ala Leu Ile Asp Asn Glu Asn Arg Asp Thr Thr Leu Gln Leu
                        610                 615                 620

Thr Asp Pro Arg Gly Thr Val Ile Gly Thr Val Ser Val Thr Val Ser
        625                 630                 635                 640

Ala Phe Asp Asp Pro Met Tyr Leu
                        645
```

<210> SEQ ID NO 21
<211> LENGTH: 120
<212> TYPE: PRT
<213> ORGANISM: Homo sapiens
<220> FEATURE:
<221> NAME/KEY: MIS_FEATURE
<222> LOCATION: 98
<223> OTHER INFORMATION: Amino acid 98 is unknown

<400> SEQUENCE: 21

Thr Phe Glu Asp Val Cys Arg Tyr Phe Thr Asp Ile Ile Lys Cys Arg
1               5                  10                  15

Val Ile Asn Thr Ser His Leu Ser Ile His Lys Thr Trp Glu Glu Ala
            20                  25                  30

Arg Leu His Gly Ala Trp Thr Leu His Glu Asp Pro Arg Gln Asn Arg
        35                  40                  45

Gly Gly Gly Cys Ile Asn His Lys Asp Thr Phe Phe Gln Asn Pro Gln
    50                  55                  60

Tyr Ile Phe Glu Val Lys Lys Pro Glu Asp Glu Val Leu Ile Cys Ile
65                  70                  75                  80

Gln Gln Arg Pro Lys Arg Ser Thr Arg Arg Glu Gly Lys Gly Glu Asn
                85                  90                  95

Leu Xaa Ile Gly Phe Asp Ile Tyr Lys Val Glu Glu Asn Arg Gln Tyr
            100                 105                 110

Arg Met His Ser Leu Gln His Lys
        115                 120

<210> SEQ ID NO 22
<211> LENGTH: 20
<212> TYPE: DNA
<213> ORGANISM: Artificial Sequence
<220> FEATURE:
<223> OTHER INFORMATION: Sequence primer

<400> SEQUENCE: 22
tcagacagcc gtgagagagg                                             20

<210> SEQ ID NO 23
<211> LENGTH: 29
<212> TYPE: DNA
<213> ORGANISM: Artificial Sequence
<220> FEATURE:
<223> OTHER INFORMATION: Sequence primer

<400> SEQUENCE: 23
tagctcgagt ggacgtaatc gtcgatgac                                   29

<210> SEQ ID NO 24
<211> LENGTH: 29
<212> TYPE: DNA
<213> ORGANISM: Artificial Sequence
<220> FEATURE:
<223> OTHER INFORMATION: Sequence primer

<400> SEQUENCE: 24
tagctcgagt gctgtaggct gtgcatacg                                   29

<210> SEQ ID NO 25
<211> LENGTH: 20
<212> TYPE: DNA
<213> ORGANISM: Artificial Sequence
<220> FEATURE:

<223> OTHER INFORMATION: Sequence primer

<400> SEQUENCE: 25
tgcacagcct acagcataag                                                   20

<210> SEQ ID NO 26
<211> LENGTH: 26
<212> TYPE: DNA
<213> ORGANISM: Artificial Sequence
<220> FEATURE:
<223> OTHER INFORMATION: Sequence primer

<400> SEQUENCE: 26
acttcatctt ctggcttctt gacttc                                            26

<210> SEQ ID NO 27
<211> LENGTH: 22
<212> TYPE: DNA
<213> ORGANISM: Artificial Sequence
<220> FEATURE:
<223> OTHER INFORMATION: Sequence primer

<400> SEQUENCE: 27
gctgcatcaa ccacaaggac ac                                                22

<210> SEQ ID NO 28
<211> LENGTH: 31
<212> TYPE: PRT
<213> ORGANISM: Homo sapiens

<400> SEQUENCE: 28

Glu Val Glu Trp Thr Gly Ala Trp Ser Asp Ser Ser Glu Trp Asn
1               5                   10                  15

Asn Val Asp Pro Tyr Glu Arg Asp Gln Leu Arg Val Lys Met Glu
                20                  25                  30

<210> SEQ ID NO 29
<211> LENGTH: 31
<212> TYPE: PRT
<213> ORGANISM: chicken

<400> SEQUENCE: 29

Glu Val Glu Trp Thr Gly Ala Trp Ser Asp Ser Ser Ser Gln Trp Asn
1               5                   10                  15

Glu Val Glu Pro Ser Leu Arg Gln Gln Ile Met Val Arg Met Glu
                20                  25                  30

<210> SEQ ID NO 30
<211> LENGTH: 32
<212> TYPE: PRT
<213> ORGANISM: Mus musculus

<400> SEQUENCE: 30

Glu Arg Glu Trp Thr Gly Pro Trp Ser Asp Thr Ser Ser Glu Trp Gln
1               5                   10                  15

Lys Val Asp Pro Tyr Glu Arg Glu Lys Met Gly Val Thr Val Gln Asp
                20                  25                  30

<210> SEQ ID NO 31
<211> LENGTH: 31
<212> TYPE: PRT
<213> ORGANISM: Homo sapiens

<400> SEQUENCE: 31

```
Glu Val Glu Trp Thr Gly Arg Trp Asn Asp Asn Cys Pro Ser Trp Asn
1               5                   10                  15

Thr Ile Asp Pro Glu Glu Arg Glu Arg Leu Thr Arg Arg His Glu
            20                  25                  30
```

<210> SEQ ID NO 32
<211> LENGTH: 31
<212> TYPE: PRT
<213> ORGANISM: chicken

<400> SEQUENCE: 32

```
Glu Val Glu Trp Thr Gly Lys Trp Asn Asp Asn Cys Pro Asn Trp Ser
1               5                   10                  15

Gly Val Asp Pro Glu Val Arg Glu Arg Leu Thr Arg Arg His Glu
            20                  25                  30
```

<210> SEQ ID NO 33
<211> LENGTH: 31
<212> TYPE: PRT
<213> ORGANISM: rat

<400> SEQUENCE: 33

```
Gln Val Glu Trp Thr Gly Lys Trp Asn Asp Asn Cys Pro Ser Trp Asn
1               5                   10                  15

Thr Val Asp Pro Glu Val Arg Ala Asn Leu Thr Glu Arg Gln Glu
            20                  25                  30
```

<210> SEQ ID NO 34
<211> LENGTH: 31
<212> TYPE: PRT
<213> ORGANISM: rabbit

<400> SEQUENCE: 34

```
Glu Val Glu Trp Thr Gly Arg Trp Asn Asp Asn Cys Pro Asn Trp Asn
1               5                   10                  15

Thr Val Asp Pro Glu Val Arg Glu Arg Leu Ala Glu Arg His Glu
            20                  25                  30
```

<210> SEQ ID NO 35
<211> LENGTH: 31
<212> TYPE: PRT
<213> ORGANISM: chicken

<400> SEQUENCE: 35

```
Gln Val Glu Trp Thr Gly Ala Trp Ser Asp Gly Ser Ser Glu Trp Asp
1               5                   10                  15

Asn Ile Asp Pro Ser Asp Arg Glu Glu Leu Gln Leu Lys Met Glu
            20                  25                  30
```

<210> SEQ ID NO 36
<211> LENGTH: 32
<212> TYPE: PRT
<213> ORGANISM: human

<400> SEQUENCE: 36

```
Gln Val Glu Trp Asn Gly Ser Trp Ser Asp Arg Trp Lys Asp Trp Ser
1               5                   10                  15

Phe Val Asp Lys Asp Glu Lys Ala Arg Leu Gln His Gln Val Thr Glu
            20                  25                  30
```

<210> SEQ ID NO 37

<211> LENGTH: 32
<212> TYPE: PRT
<213> ORGANISM: mouse

<400> SEQUENCE: 37

Gln Val Glu Trp Asn Gly Ser Trp Ser Asp Gly Trp Lys Asp Trp Ser
1               5                   10                  15

Phe Val Asp Lys Asp Glu Lys Ala Arg Leu Gln His Gln Val Thr Glu
            20                  25                  30

<210> SEQ ID NO 38
<211> LENGTH: 32
<212> TYPE: PRT
<213> ORGANISM: chicken

<400> SEQUENCE: 38

Gln Val Glu Trp Asn Gly Pro Trp Ser Asp Lys Ser Glu Glu Trp Asn
1               5                   10                  15

Phe Ile Asp Glu Glu Glu Lys Ile Arg Leu Gln His Lys Ile Ala Glu
            20                  25                  30

<210> SEQ ID NO 39
<211> LENGTH: 32
<212> TYPE: PRT
<213> ORGANISM: pig

<400> SEQUENCE: 39

Gln Val Glu Trp Asn Gly Ser Trp Ser Asp Ser Trp Lys Asp Trp Ser
1               5                   10                  15

Phe Val Asp Lys Asp Glu Lys Ala Arg Leu Gln His Gln Val Thr Glu
            20                  25                  30

<210> SEQ ID NO 40
<211> LENGTH: 32
<212> TYPE: PRT
<213> ORGANISM: rat

<400> SEQUENCE: 40

Gln Val Glu Trp Asn Gly Ser Trp Ser Asp Gly Trp Lys Asp Trp Ser
1               5                   10                  15

Phe Val Asp Lys Asp Glu Lys Ala Arg Leu Gln His Gln Val Thr Glu
            20                  25                  30

<210> SEQ ID NO 41
<211> LENGTH: 32
<212> TYPE: PRT
<213> ORGANISM: cow

<400> SEQUENCE: 41

Gln Val Glu Trp Asn Gly Ser Trp Ser Asp Ser Trp Lys Asp Trp Ser
1               5                   10                  15

Tyr Val Asp Lys Asp Glu Lys Ala Arg Leu Gln His Gln Val Thr Glu
            20                  25                  30

<210> SEQ ID NO 42
<211> LENGTH: 31
<212> TYPE: PRT
<213> ORGANISM: rat

<400> SEQUENCE: 42

Glu Val Glu Trp Ser Gly Ala Trp Ser Asp Asn Ala Pro Glu Trp Asn
1               5                   10                  15

Tyr Ile Asp Pro Arg Arg Lys Glu Glu Leu Asp Lys Lys Ala Glu
             20                  25                  30

<210> SEQ ID NO 43
<211> LENGTH: 33
<212> TYPE: PRT
<213> ORGANISM: Drosophila melanogaster

<400> SEQUENCE: 43

Asn Glu Ala Glu Trp Asn Gly Pro Trp Ser Asp Ser Pro Glu Trp
1               5                   10                  15

Arg Tyr Ile Pro Glu Glu Gln Lys Ala Glu Ile Gly Leu Thr Phe Asp
             20                  25                  30

Arg

<210> SEQ ID NO 44
<211> LENGTH: 36
<212> TYPE: PRT
<213> ORGANISM: Caenorhabditis elegans

<400> SEQUENCE: 44

Glu Lys Glu Trp Asn Gly Ala Trp Ser Asp Asp Ser Pro Glu Trp Gln
1               5                   10                  15

Asn Val Ser Ala Ser Gln Leu Ser Thr Met Gly Val Gln Pro Ala Asn
             20                  25                  30

Ser Asp Ser Asp
         35

<210> SEQ ID NO 45
<211> LENGTH: 32
<212> TYPE: PRT
<213> ORGANISM: Caenorhabditis elegans

<400> SEQUENCE: 45

Glu Gln Glu Trp Asn Gly Pro Trp Ser Asp Asn Ser Arg Glu Trp Arg
1               5                   10                  15

Ser Val Pro Asp Ser Val Lys Gln Asp Met Gly Leu Lys Phe Asp His
             20                  25                  30

<210> SEQ ID NO 46
<211> LENGTH: 700
<212> TYPE: PRT
<213> ORGANISM: mouse

<400> SEQUENCE: 46

Met Ala Gly Ile Ala Ile Lys Leu Ala Lys Asp Arg Glu Ala Ala Glu
1               5                   10                  15

Gly Leu Gly Ser His Glu Arg Ala Ile Lys Tyr Leu Asn Gln Asp Tyr
             20                  25                  30

Glu Thr Leu Arg Asn Glu Cys Leu Glu Ala Gly Ala Leu Phe Gln Asp
         35                  40                  45

Pro Ser Phe Pro Ala Leu Pro Ser Ser Leu Gly Tyr Lys Glu Leu Gly
     50                  55                  60

Pro Tyr Ser Ser Lys Thr Arg Gly Ile Glu Trp Lys Arg Pro Thr Glu
65                  70                  75                  80

Ile Cys Ala Asp Pro Gln Phe Ile Ile Gly Gly Ala Thr Arg Thr Asp
                 85                  90                  95

Ile Cys Gln Gly Ala Leu Gly Asp Cys Trp Leu Leu Ala Ala Ile Ala
             100                 105                 110

```
Ser Leu Thr Leu Asn Glu Glu Ile Leu Ala Arg Val Val Pro Pro Asp
        115                 120                 125

Gln Ser Phe Gln Glu Asn Tyr Ala Gly Ile Phe His Phe Gln Phe Trp
    130                 135                 140

Gln Tyr Gly Glu Trp Val Glu Val Val Val Asp Asp Arg Leu Pro Thr
145                 150                 155                 160

Lys Asp Gly Glu Leu Leu Phe Val His Ser Ala Glu Gly Ser Glu Phe
                165                 170                 175

Trp Ser Ala Leu Leu Glu Lys Ala Tyr Ala Lys Ile Asn Gly Cys Tyr
            180                 185                 190

Glu Thr Leu Ser Gly Gly Ala Thr Thr Glu Gly Phe Glu Asp Phe Thr
        195                 200                 205

Gly Gly Ile Ala Glu Trp Tyr Glu Leu Arg Lys Pro Pro Asn Leu
    210                 215                 220

Phe Lys Ile Ile Gln Lys Ala Leu Glu Lys Gly Ser Leu Leu Gly Cys
225                 230                 235                 240

Ser Ile Asp Ile Thr Ser Ala Ala Asp Ser Glu Ala Val Thr Tyr Gln
                245                 250                 255

Lys Leu Val Lys Gly His Ala Tyr Ser Val Thr Gly Ala Glu Glu Val
            260                 265                 270

Glu Ser Ser Gly Ser Leu Gln Lys Leu Ile Arg Leu Ala Asn Pro Trp
        275                 280                 285

Gly Gln Val Glu Trp Thr Gly Lys Trp Asn Asp Asn Cys Pro Ser Trp
    290                 295                 300

Asn Thr Val Asp Pro Glu Val Arg Ala Asn Leu Thr Glu Arg Gln Glu
305                 310                 315                 320

Asp Gly Glu Phe Trp Met Ser Phe Ser Asp Phe Leu Arg His Tyr Ser
                325                 330                 335

Arg Leu Glu Ile Cys Asn Leu Thr Pro Asp Thr Leu Thr Cys Asp Ser
            340                 345                 350

Tyr Lys Lys Trp Lys Leu Thr Lys Met Asp Gly Asn Trp Arg Arg Gly
        355                 360                 365

Ser Thr Ala Gly Gly Cys Arg Asn Tyr Pro Asn Thr Phe Trp Met Asn
    370                 375                 380

Pro Gln Tyr Leu Ile Lys Leu Glu Glu Glu Asp Glu Asp Glu Glu Asp
385                 390                 395                 400

Gly Gly Arg Gly Cys Thr Phe Leu Val Gly Leu Ile Gln Lys His Arg
                405                 410                 415

Arg Arg Gln Arg Lys Met Gly Glu Asp Met His Thr Ile Gly Phe Gly
            420                 425                 430

Ile Tyr Glu Val Pro Glu Glu Leu Thr Gly Gln Thr Asn Ile His Leu
        435                 440                 445

Gly Lys Asn Phe Phe Leu Thr Thr Arg Ala Arg Glu Arg Ser Asp Thr
    450                 455                 460

Phe Ile Asn Leu Arg Glu Val Leu Asn Arg Phe Lys Leu Pro Pro Gly
465                 470                 475                 480

Glu Tyr Val Leu Val Pro Ser Thr Phe Glu Pro His Lys Asp Gly Asp
                485                 490                 495

Phe Asp Ile Arg Val Phe Ser Glu Lys Lys Ala Asp Tyr Gln Ala Val
            500                 505                 510

Asp Asp Glu Ile Glu Ala Asn Ile Glu Glu Ile Asp Ala Asn Glu Glu
        515                 520                 525

Asp Ile Asp Asp Gly Phe Arg Arg Leu Phe Val Gln Leu Ala Gly Glu
```

-continued

```
                530                 535                 540
Asp Ala Glu Ile Ser Ala Phe Glu Leu Gln Thr Ile Leu Arg Arg Val
545                 550                 555                 560

Leu Ala Lys Arg Gln Asp Ile Lys Ser Asp Gly Phe Ser Ile Glu Thr
                565                 570                 575

Cys Lys Ile Met Val Asp Met Leu Asp Glu Asp Gly Ser Gly Lys Leu
                580                 585                 590

Gly Leu Lys Glu Phe Tyr Ile Leu Trp Thr Lys Ile Gln Lys Tyr Gln
                595                 600                 605

Lys Ile Tyr Arg Glu Ile Asp Val Asp Arg Ser Gly Thr Met Asn Ser
                610                 615                 620

Tyr Glu Met Arg Lys Ala Leu Glu Glu Ala Gly Phe Lys Leu Pro Cys
625                 630                 635                 640

Gln Leu His Gln Val Ile Val Ala Arg Phe Ala Asp Asp Glu Leu Ile
                645                 650                 655

Ile Asp Phe Asp Asn Phe Val Arg Cys Leu Val Arg Leu Glu Thr Leu
                660                 665                 670

Phe Lys Ile Phe Lys Gln Leu Asp Pro Glu Asn Thr Gly Thr Ile Gln
                675                 680                 685

Leu Asn Leu Ala Ser Trp Leu Ser Phe Ser Val Leu
                690                 695                 700

<210> SEQ ID NO 47
<211> LENGTH: 714
<212> TYPE: PRT
<213> ORGANISM: human

<400> SEQUENCE: 47

Met Ser Glu Glu Ile Ile Thr Pro Val Tyr Cys Thr Gly Val Ser Ala
1                   5                   10                  15

Gln Val Gln Lys Gln Arg Ala Arg Glu Leu Gly Leu Gly Arg His Glu
                20                  25                  30

Asn Ala Ile Lys Tyr Leu Gly Gln Asp Tyr Glu Gln Leu Arg Val Arg
            35                  40                  45

Cys Leu Gln Ser Gly Thr Leu Phe Arg Asp Glu Ala Phe Pro Pro Val
50                  55                  60

Pro Gln Ser Leu Gly Tyr Lys Asp Leu Gly Pro Asn Ser Ser Lys Thr
65                  70                  75                  80

Tyr Gly Ile Lys Trp Lys Arg Pro Thr Glu Leu Leu Ser Asn Pro Gln
                85                  90                  95

Phe Ile Val Asp Gly Ala Thr Arg Thr Asp Ile Cys Gln Gly Ala Leu
            100                 105                 110

Gly Asp Cys Trp Leu Leu Ala Ala Ile Ala Ser Leu Thr Leu Asn Asp
        115                 120                 125

Thr Leu Leu His Arg Val Val Pro His Gly Gln Ser Phe Gln Asn Gly
    130                 135                 140

Tyr Ala Gly Ile Phe His Phe Gln Leu Trp Gln Phe Gly Glu Trp Val
145                 150                 155                 160

Asp Val Val Val Asp Asp Leu Leu Pro Ile Lys Asp Gly Lys Leu Val
                165                 170                 175

Phe Val His Ser Ala Glu Gly Asn Glu Phe Trp Ser Ala Leu Leu Glu
            180                 185                 190

Lys Ala Tyr Ala Lys Val Asn Gly Ser Tyr Glu Ala Leu Ser Gly Gly
        195                 200                 205
```

```
Ser Thr Ser Glu Gly Phe Glu Asp Phe Thr Gly Val Thr Glu Trp
    210                 215                 220

Tyr Glu Leu Arg Lys Ala Pro Ser Asp Leu Tyr Gln Ile Ile Leu Lys
225                 230                 235                 240

Ala Leu Glu Arg Gly Ser Leu Leu Gly Cys Ser Ile Asp Ile Ser Ser
                245                 250                 255

Val Leu Asp Met Glu Ala Ile Thr Phe Lys Lys Leu Val Lys Gly His
            260                 265                 270

Ala Tyr Ser Val Thr Gly Ala Lys Gln Val Asn Tyr Arg Gly Gln Val
        275                 280                 285

Val Ser Leu Ile Arg Met Ala Asn Pro Trp Gly Glu Val Glu Trp Thr
    290                 295                 300

Gly Ala Trp Ser Asp Ser Ser Glu Trp Asn Asn Val Asp Pro Tyr
305                 310                 315                 320

Glu Arg Asp Gln Leu Arg Val Lys Met Glu Asp Gly Glu Phe Trp Met
                325                 330                 335

Ser Phe Arg Asp Phe Met Arg Glu Phe Thr Arg Leu Glu Ile Cys Asn
            340                 345                 350

Leu Thr Pro Asp Ala Leu Lys Ser Arg Thr Ile Arg Lys Trp Asn Thr
        355                 360                 365

Thr Leu Tyr Glu Gly Pro Trp Arg Arg Gly Ser Thr Ala Gly Gly Cys
    370                 375                 380

Arg Asn Tyr Pro Ala Thr Ser Trp Val Asn Pro Gln Phe Lys Ile Arg
385                 390                 395                 400

Leu Asp Glu Thr Asp Asp Pro Asp Tyr Gly Asp Arg Glu Ser Gly
                405                 410                 415

Cys Ser Phe Val Leu Ala Leu Met Gln Lys His Arg Arg Glu Arg
            420                 425                 430

Arg Phe Gly Arg Asp Met Glu Thr Ile Gly Phe Ala Val Tyr Glu Val
        435                 440                 445

Pro Pro Glu Leu Val Gly Gln Pro Ala Val His Leu Lys Arg Asp Phe
450                 455                 460

Phe Leu Ala Asn Ala Ser Arg Ala Arg Ser Glu Gln Phe Ile Asn Leu
465                 470                 475                 480

Arg Glu Val Ser Thr Arg Phe Arg Leu Pro Pro Gly Glu Tyr Val Val
                485                 490                 495

Val Pro Ser Thr Phe Glu Pro Asn Lys Glu Gly Asp Phe Val Leu Arg
            500                 505                 510

Phe Phe Ser Glu Lys Ser Ala Gly Thr Val Glu Leu Asp Asp Gln Ile
        515                 520                 525

Gln Ala Asn Leu Pro Asp Glu Gln Val Leu Ser Glu Glu Ile Asp
    530                 535                 540

Glu Asn Phe Lys Ala Leu Phe Arg Gln Leu Ala Gly Glu Asp Met Glu
545                 550                 555                 560

Ile Ser Val Lys Glu Leu Arg Thr Ile Leu Asn Arg Ile Ile Ser Lys
                565                 570                 575

Arg Lys Asp Leu Arg Thr Lys Gly Phe Ser Leu Glu Ser Cys Arg Ser
            580                 585                 590

Met Val Asn Leu Met Asp Arg Asp Gly Asn Gly Lys Leu Gly Leu Val
        595                 600                 605

Glu Phe Asn Ile Leu Trp Asn Arg Ile Arg Asn Tyr Leu Ser Ile Phe
    610                 615                 620

Arg Lys Phe Asp Leu Asp Lys Ser Gly Ser Met Ser Ala Tyr Glu Met
```

```
                625                 630                 635                 640
Arg Met Ala Ile Glu Ser Ala Gly Phe Lys Leu Asn Lys Leu Tyr
                    645                 650                 655
Glu Leu Ile Ile Thr Arg Tyr Ser Glu Pro Asp Leu Ala Val Asp Phe
                    660                 665                 670
Asp Asn Phe Val Cys Cys Leu Val Arg Leu Glu Thr Met Phe Arg Phe
                675                 680                 685
Phe Lys Thr Leu Asp Thr Asp Leu Asp Gly Val Val Thr Phe Asp Leu
            690                 695                 700
Phe Lys Trp Leu Gln Leu Thr Met Phe Ala
705                 710

<210> SEQ ID NO 48
<211> LENGTH: 821
<212> TYPE: PRT
<213> ORGANISM: mouse

<400> SEQUENCE: 48

Met Pro Thr Val Ile Ser Pro Thr Val Ala Pro Arg Thr Gly Ala Glu
1               5                   10                  15
Pro Arg Ser Pro Gly Pro Val Pro His Pro Ala Gln Gly Lys Thr Thr
                20                  25                  30
Glu Ala Gly Gly Gly His Pro Ser Gly Ile Tyr Ser Ala Ile Ile Ser
            35                  40                  45
Arg Asn Phe Pro Ile Ile Gly Val Lys Glu Lys Thr Arg Glu Gln Leu
        50                  55                  60
Arg Lys Lys Cys Leu Glu Lys Val Leu Phe Tyr Leu Asp Pro Glu Phe
65                  70                  75                  80
Pro Pro Asp Glu Thr Ser Leu Phe Tyr Ser Gln Lys Phe Pro Ile Gln
                85                  90                  95
Phe Val Trp Lys Arg Pro Pro Glu Ile Cys Glu Asn Pro Arg Phe Ile
                100                 105                 110
Ile Gly Gly Ala Asn Arg Thr Asp Ile Cys Gln Gly Asp Leu Gly Asp
            115                 120                 125
Cys Trp Phe Leu Ala Ala Ile Ala Cys Leu Thr Leu Asn Glu Arg Leu
130                 135                 140
Leu Phe Arg Val Ile Pro His Asp Gln Ser Phe Thr Glu Asn Tyr Ala
145                 150                 155                 160
Gly Ile Phe His Phe Gln Phe Trp Arg Tyr Gly Asp Trp Val Asp Val
                165                 170                 175
Val Ile Asp Asp Cys Leu Pro Thr Tyr Asn Asn Gln Leu Val Phe Thr
            180                 185                 190
Lys Ser Asn His Arg Asn Glu Phe Trp Ser Ala Leu Leu Glu Lys Ala
        195                 200                 205
Tyr Ala Lys Leu His Gly Ser Tyr Glu Ala Leu Lys Gly Gly Asn Thr
    210                 215                 220
Thr Glu Ala Met Glu Asp Phe Thr Gly Val Thr Glu Phe Phe Glu
225                 230                 235                 240
Ile Lys Asp Ala Pro Ser Asp Met Tyr Lys Ile Met Arg Lys Ala Ile
                245                 250                 255
Glu Arg Gly Ser Leu Met Gly Cys Ser Ile Asp Asp Gly Thr Asn Met
            260                 265                 270
Thr Tyr Gly Thr Ser Pro Ser Gly Leu Asn Met Gly Glu Leu Ile Ala
        275                 280                 285
```

```
Arg Met Val Arg Asn Met Asp Asn Ser Leu Leu Arg Asp Ser Asp Leu
        290                 295                 300

Asp Pro Arg Gly Ser Asp Asp Arg Pro Ser Arg Thr Ile Val Pro Val
305                 310                 315                 320

Gln Tyr Glu Thr Arg Met Ala Cys Gly Leu Val Lys Gly His Ala Tyr
                    325                 330                 335

Ser Val Thr Gly Leu Glu Glu Ala Leu Phe Lys Gly Glu Lys Val Lys
                340                 345                 350

Leu Val Arg Leu Ala Asn Pro Trp Gly Gln Val Glu Trp Asn Gly Ser
            355                 360                 365

Trp Ser Asp Gly Trp Lys Asp Trp Ser Phe Val Asp Lys Asp Glu Lys
        370                 375                 380

Ala Arg Leu Gln Lys Gln Val Thr Glu Asp Gly Glu Phe Trp Met Ser
385                 390                 395                 400

Tyr Asp Asp Phe Val Tyr His Phe Thr Lys Leu Glu Ile Cys Asn Leu
                    405                 410                 415

Thr Ala Asp Ala Leu Glu Ser Asp Lys Leu Gln Lys Thr Thr Val Ser
                420                 425                 430

Val Asn Glu Gly Arg Trp Val Arg Gly Cys Ser Ala Gly Gly Cys Arg
            435                 440                 445

Asn Phe Pro Asp Thr Phe Trp Thr Asn Pro Gln Tyr Arg Leu Lys Leu
        450                 455                 460

Leu Glu Glu Asp Asp Pro Glu Asp Ser Glu Val Ile Cys Ser Phe
465                 470                 475                 480

Leu Val Ala Leu Met Cys Lys Asn Arg Arg Lys Asp Arg Lys Leu Gly
                485                 490                 495

Ala Asn Leu Phe Thr Ile Gly Phe Ala Ile Tyr Glu Val Pro Lys Glu
                500                 505                 510

Met His Gly Asn Lys Gln His Leu Gln Lys Asp Phe Pro Leu Tyr Asn
            515                 520                 525

Ala Ser Lys Ala Arg Ser Lys Thr Tyr Ile Asn Met Arg Glu Val Ser
        530                 535                 540

Gln Arg Phe Arg Leu Pro Pro Ser Glu Tyr Val Ile Val Pro Ser Thr
545                 550                 555                 560

Tyr Glu Pro His Gln Glu Gly Glu Phe Ile Leu Arg Val Phe Ser Glu
                565                 570                 575

Lys Arg Asn Leu Ser Glu Glu Ala Glu Asn Thr Ile Ser Val Asp Arg
                580                 585                 590

Pro Val Lys Lys Lys Asn Lys Pro Ile Ile Phe Val Ser Asp Arg
        595                 600                 605

Ala Asn Ser Asn Lys Glu Leu Gly Val Asp Gln Glu Ala Glu Glu Gly
        610                 615                 620

Lys Asp Lys Ala Gly Pro Glu Lys Arg Gly Glu Thr Pro Gln Pro Arg
625                 630                 635                 640

Pro Gly His Thr Asp Gln Glu Ser Glu Glu Gln Gln Phe Arg Asn
                645                 650                 655

Ile Phe Arg Gln Ile Ala Gly Asp Asp Met Glu Ile Cys Ala Asp Glu
                660                 665                 670

Leu Lys Asn Val Leu Asn Thr Val Val Asn Lys His Lys Asp Leu Lys
            675                 680                 685

Thr Gln Gly Phe Thr Leu Glu Ser Cys Arg Ser Met Ile Ala Leu Met
        690                 695                 700

Asp Thr Asp Gly Ser Gly Arg Leu Asn Leu Gln Glu Phe His His Leu
```

-continued

```
            705                 710                 715                 720
Trp Lys Lys Ile Lys Ala Trp Gln Lys Ile Phe Lys His Tyr Asp Thr
                725                 730                 735
Asp His Ser Gly Thr Ile Asn Ser Tyr Glu Met Arg Asn Ala Val Asn
                740                 745                 750
Asp Ala Gly Phe His Leu Asn Ser Gln Leu Tyr Asp Ile Ile Thr Met
                755                 760                 765
Arg Tyr Ala Asp Lys His Met Asn Ile Asp Phe Asp Ser Phe Ile Cys
                770                 775                 780
Cys Phe Val Arg Leu Glu Gly Met Phe Arg Ala Phe Asn Ala Phe Asp
785                 790                 795                 800
Lys Asp Gly Asp Gly Ile Ile Lys Leu Asn Val Leu Glu Trp Leu Gln
                805                 810                 815
Leu Thr Met Tyr Ala
                820

<210> SEQ ID NO 49
<211> LENGTH: 703
<212> TYPE: PRT
<213> ORGANISM: rat

<400> SEQUENCE: 49

Met Ala Ala Leu Ala Ala Gly Val Ser Lys Gln Arg Ala Val Ala Glu
1               5                   10                  15
Gly Leu Gly Ser Asn Gln Asn Ala Val Lys Tyr Leu Gly Gln Asp Phe
                20                  25                  30
Glu Thr Leu Arg Lys Gln Cys Leu Asn Ser Gly Val Leu Phe Lys Asp
                35                  40                  45
Pro Glu Phe Pro Ala Cys Pro Ser Ala Leu Gly Tyr Lys Asp Leu Gly
                50                  55                  60
Pro Gly Ser Pro Asp Thr Gln Gly Ile Val Trp Lys Arg Pro Thr Glu
65                  70                  75                  80
Leu Cys Pro Asn Pro Gln Phe Ile Val Gly Gly Ala Thr Arg Thr Asp
                85                  90                  95
Ile Arg Gln Gly Gly Leu Val Asp Cys Trp Leu Leu Ala Ala Ile Ala
                100                 105                 110
Ser Leu Thr Leu Asn Glu Lys Leu Leu Tyr Arg Val Leu Pro Arg Asp
                115                 120                 125
Gln Ser Phe Gln Lys Asp Tyr Ala Gly Ile Phe His Phe Gln Phe Trp
                130                 135                 140
Gln Tyr Gly Glu Trp Val Glu Val Ile Asp Asp Arg Leu Pro Thr
145                 150                 155                 160
Lys Asn Gly Gln Leu Leu Phe Leu His Ser Glu Gly Asn Glu Phe
                165                 170                 175
Trp Ser Ala Leu Leu Glu Lys Ala Tyr Ala Lys Leu Asn Gly Ser Tyr
                180                 185                 190
Glu Ala Leu Val Gly Gly Ser Thr Ile Glu Gly Phe Glu Asp Phe Thr
                195                 200                 205
Gly Gly Ile Ser Glu Phe Tyr Asp Leu Lys Lys Pro Pro Glu Asn Leu
                210                 215                 220
Tyr Tyr Ile Ile Gln Lys Ala Leu Ala Lys Gly Ser Leu Leu Gly Cys
225                 230                 235                 240
Ser Ile Asp Val Ser Thr Ala Ala Glu Ala Glu Ala Thr Thr Arg Gln
                245                 250                 255
```

-continued

```
Lys Leu Val Lys Gly His Ala Tyr Ser Val Thr Gly Val Glu Glu Val
            260                 265                 270

Asn Phe Lys Gly Arg Pro Glu Lys Leu Ile Arg Leu Ala Asn Pro Trp
            275                 280                 285

Gly Glu Val Glu Trp Ser Gly Ala Trp Ser Asp Asn Ala Pro Glu Trp
            290                 295                 300

Asn Tyr Ile Asp Pro Arg Arg Lys Glu Glu Leu Asp Lys Lys Ala Glu
305                 310                 315                 320

Asp Gly Glu Phe Trp Met Ser Phe Ser Asp Phe Leu Lys Gln Tyr Ser
                    325                 330                 335

Arg Leu Glu Ile Cys Asn Leu Ser Pro Asp Ser Leu Ser Ser Glu Glu
            340                 345                 350

Ile His Lys Trp Asn Leu Val Leu Phe Asn Gly Arg Trp Thr Arg Gly
            355                 360                 365

Ser Thr Ala Gly Gly Cys Leu Asn Tyr Pro Gly Thr Tyr Trp Thr Asn
            370                 375                 380

Pro Gln Phe Lys Ile His Leu Asp Glu Val Asp Glu Asp Gln Glu Glu
385                 390                 395                 400

Gly Thr Ser Glu Pro Cys Cys Thr Val Leu Leu Gly Leu Met Cys Lys
                    405                 410                 415

Asn Arg Arg Arg Gln Lys Arg Ile Gly Gln Gly Met Leu Ser Ile Gly
            420                 425                 430

Tyr Ala Val Tyr Gln Ile Pro Lys Glu Leu Glu Ser His Thr Asp Ala
            435                 440                 445

His Leu Gly Arg Asp Phe Phe Leu Gly Arg Gln Pro Ser Thr Cys Ser
            450                 455                 460

Ser Thr Tyr Met Asn Leu Arg Glu Val Ser Ser Arg Val Arg Leu Pro
465                 470                 475                 480

Pro Gly Gln Tyr Leu Val Val Pro Ser Thr Phe Glu Pro Phe Lys Asp
                    485                 490                 495

Gly Asp Phe Cys Leu Arg Val Phe Ser Glu Lys Lys Ala Lys Ala Leu
            500                 505                 510

Glu Ile Gly Asp Thr Val Ser Gly His Pro His Glu Pro His Pro Arg
            515                 520                 525

Asp Met Asp Glu Glu Asp Glu His Val Arg Ser Leu Phe Glu Glu Phe
            530                 535                 540

Val Gly Lys Asp Ser Glu Ile Ser Ala Asn Gln Leu Lys Arg Val Leu
545                 550                 555                 560

Asn Glu Val Leu Ser Lys Arg Thr Asp His Lys Phe Asp Gly Phe Asn
                    565                 570                 575

Val Asn Thr Cys Arg Glu Met Ile Ser Leu Leu Asp Ser Asp Gly Thr
            580                 585                 590

Gly Ser Leu Gly Pro Met Glu Phe Lys Thr Leu Trp Leu Lys Ile Arg
            595                 600                 605

Thr Tyr Leu Glu Ile Phe Gln Glu Met Asp His Asn His Val Gly Thr
            610                 615                 620

Ile Glu Ala His Glu His Arg Thr Ala Leu Lys Lys Ala Gly Pro Thr
625                 630                 635                 640

Leu Asn Asn Gln Val Gln Gln Thr Ile Ala Met Arg Tyr Ala Cys Ser
                    645                 650                 655

Lys Leu Gly Val Asp Phe Asn Gly Phe Val Ala Cys Met Ile Arg Leu
            660                 665                 670

Glu Thr Leu Phe Lys Leu Phe Arg Leu Leu Asp Lys Asp Gln Asn Gly
```

-continued

```
        675                 680                 685

Ile Val Gln Leu Ser Leu Ala Glu Trp Leu Cys Cys Val Leu Val
    690                 695                 700
```